United States Patent
Schacht et al.

(10) Patent No.: US 7,005,123 B1
(45) Date of Patent: Feb. 28, 2006

(54) FUNCTIONAL POLY-α-AMINO-ACID DERIVATIVES USEFUL FOR THE MODIFICATION OF BIOLOGICALLY ACTIVE MATERIALS AND THEIR APPLICATION

(75) Inventors: Etienne Honoré Schacht, Staden (BE); Veska Toncheva, Ghent (BE)

(73) Assignee: Universiteit Gent, Ghent (BE)

( * ) Notice: Subject to any disclaimer, the term of this patent is extended or adjusted under 35 U.S.C. 154(b) by 593 days.

(21) Appl. No.: 10/009,808

(22) PCT Filed: Jun. 19, 2000

(86) PCT No.: PCT/BE00/00066

§ 371 (c)(1),
(2), (4) Date: Apr. 12, 2002

(87) PCT Pub. No.: WO00/78791

PCT Pub. Date: Dec. 28, 2000

(30) Foreign Application Priority Data

Jun. 17, 1999 (EP) .......................... 99870125

(51) Int. Cl.
| | |
|---|---|
| A61K 7/11 | (2006.01) |
| A61F 2/02 | (2006.01) |
| C08G 69/10 | (2006.01) |
| C08G 63/91 | (2006.01) |
| C08G 69/48 | (2006.01) |

(52) U.S. Cl. ................... 424/70.17; 424/423; 528/328; 528/363; 525/419; 525/420

(58) Field of Classification Search ................ 424/423, 424/70.17; 525/419, 420; 528/328, 363
See application file for complete search history.

(56) References Cited

FOREIGN PATENT DOCUMENTS

| | | |
|---|---|---|
| GB | 781202 | 8/1954 |
| WO | WO 97/36616 A2 | 10/1997 |
| WO | WO 98/19710 | * 11/1997 |
| WO | WO 98/19710 A2 | 5/1998 |

OTHER PUBLICATIONS

Gonsalves, "Synthesis and Properties of Degradable Polyamid and Related Polymers", TRIP, vol. 4, No. 1, 1/96, pp 25–31.

* cited by examiner

*Primary Examiner*—Carlos A. Azpuru
(74) *Attorney, Agent, or Firm*—Barnes & Thornburg

(57) ABSTRACT

A linear poly-α-amino-acid derivative has at least glutamic or aspartic or serinic repeating units and additionally having a functional group at one or both ends of the polymer backbone and/or only a single functional group as a side group on the polymer backbone, the said functional end group and/or side group being other than alcohol. The said functional derivative is useful for the modification of biologically active materials.

22 Claims, 2 Drawing Sheets

N-protected TCEG-NCA

FUNCTIONAL POLY-α-AMINO-ACID DERIVATIVES USEFUL FOR THE MODIFICATION OF BIOLOGICALLY ACTIVE MATERIALS AND THEIR APPLICATION

The present invention relates to the preparation of novel functional poly-α-amino-acid derivatives which are useful namely for the modification of biomolecules and the surface modification of biomaterials. It also relates to modified synthetic vectors useful for gene delivery which are obtainable from the said novel functional poly-α-amino-acid derivatives. The invention additionally relates to antibodies and to various therapeutic agents modified by the said novel functional poly-α-amino-acid derivatives. It also encompasses increasing plasma circulation time and decreasing immunogeneicity when administering such modified antibodies and therapeutic agents to patients. The invention thus pertains to the fields of chemical modification of bioactive molecules and biomaterial science. Finally, the present invention relates to biodegradable articles comprising at least a polymer sequence derived from the said novel functional poly-α-amino-acid derivatives.

BACKGROUND OF THE INVENTION

In the past decades there has been a great interest in the use of end group functionalized polyethylene glycol for the modification of peptides, proteins, enzymes and non-peptide drugs. For instance, A. Abuchowski et al. in *J. Biol. Chem.*, 252, 3578–3581 (1977) and in *Cancer Biochem. Biophys.*, 7, 175–186 (1984) described modifying a protein by means of polyethylene glycol grafted onto amino side groups along the said protein. It was shown by S. Zalipsky, Bioconjugate Chem. 6, 150–165 (1995) and by C. Delgado et al., *Critical Reviews in Therapeutic Drug Carrier Systems*, 9, (3,4), 249–304 (1992) that polyethylene glycol grafted proteins exhibit a longer plasma half-life in vivo, are less immunogenic and more thermostable.

Zalipsky (cited above), Delgado (cited above), T. M. Allen et al. in *Biochimica et Biophysica Acta*, 1237, 99–108 (1995), J. M. Harris, Ed. Poly(Ethylene Glycol) *Chemistry: Biotechnical and Biomedical Applications*, ed., Plenum Press, New York, 1992, and G. Hooftman et al. in *J. Bioact. Biocomp. Polymers*, 11, 135–159 (1996) have reviewed a variety of methods for introducing reactive groups at the chain end of polyethylene glycol which can react in a selective manner with protein functional side groups such as amino, thiol, guanidyl and the like.

Recently, polyethylene glycol has been used for the modification of synthetic vectors for gene delivery in order to prevent complexes with DNA from interactions with plasma proteins and erythrocytes and from enzymatic degradation in extra- and intracellular compartments (see for instance M. Ogris et al., *Gene Therapy* (1999) 6:595–605).

In biomaterial science, grafting of a polymer material surface with polyethylene glycol chains (hereinafter referred to as "PEG-ylation") has been extensively described as a method for improving surface biocompatibility. Surface PEG-ylation can be achieved by chemical grafting of polyethylene glycol onto a pre-formed surface as well as by applying a polymer having polyethylene glycol as a building part of its backbone or alternatively as a grafted side group. Such polymers can be used as a core material or be applied as a surface coating.

Polyethylene glycol is a rather stable polymer which is a repellent of protein adhesion and which is not subject to enzymatic or hydrolytic degradation under physiological conditions. However, biomedical applications are at every time looking for improved biocompatible polymeric materials. In particular, there is concern that polyethylene glycol, being not biodegradable, has difficulties to escape from cells and could be stored in cells, according to J. Lloyd, *Biochem.J.*, 261, 451–456 (1989). Therefore there is a need in the art for substituting polyethylene glycol, in such biomedical applications, by a polymer having similar properties but which is biodegradable. In another area, there is a need for the permanent grafting of polymer chains onto a polymer material surface. The above mentioned problems will be solved by the polymer and copolymer derivatives as described in this invention, containing functionalities that can be used to attach bioactive substances, e.g. short peptide molecules such as the tripeptide RGD (arginine-glycine-aspartic acid) and the like, or saccharides and oligosaccharides such as mannose and galactose. In yet another area, an object of the present invention is to provide improved synthetic vectors to serve as carrier vehicles for efficient and effective delivery of nucleic acid material, and transfection of target cells, especially in connection with gene therapy or even possibly in connection with development of DNA vaccines.

SUMMARY OF THE INVENTION

In a first aspect, the present invention provides novel poly-α-amino-acid derivatives, preferably water-soluble poly-α-amino-acid derivatives, having a functional (i.e. reactive) group at one or both ends of the polymer backbone and/or only a single functional group as a side group on the polymer backbone, the said functional end group and/or side group being other than alcohol. In a second aspect, the present invention provides a method for preparing such novel poly-α-amino-acid derivatives. In a third aspect, the present invention provides the use of such novel poly-α-amino-acid derivatives for the modification of a biologically-active ingredient such as a drug, a peptide, a protein, an enzyme, an antibody, or the like, as well as the result of such a modification, e.g. the reaction product of coupling such a novel poly-α-amino-acid derivative together with such a biologically-active (for instance therapeutic) ingredient. In a fourth aspect, the present invention provides the use of a synthetic vector modified by means of such a novel poly-α-amino-acid derivative for gene delivery. In a fifth aspect, the present invention provides improved methods of treatment of patients including the administration of therapeutic active ingredients modified by means of such novel poly-α-amino-acid derivatives. In a sixth aspect, the present invention provides biodegradable articles comprising at least a polymer sequence derived from the said novel functional poly-α-amino-acid derivatives and optionally one or more polymer sequences derived from monomers co-polymerizable therewith.

DETAILED DESCRIPTION OF THE INVENTION

Figure 1:
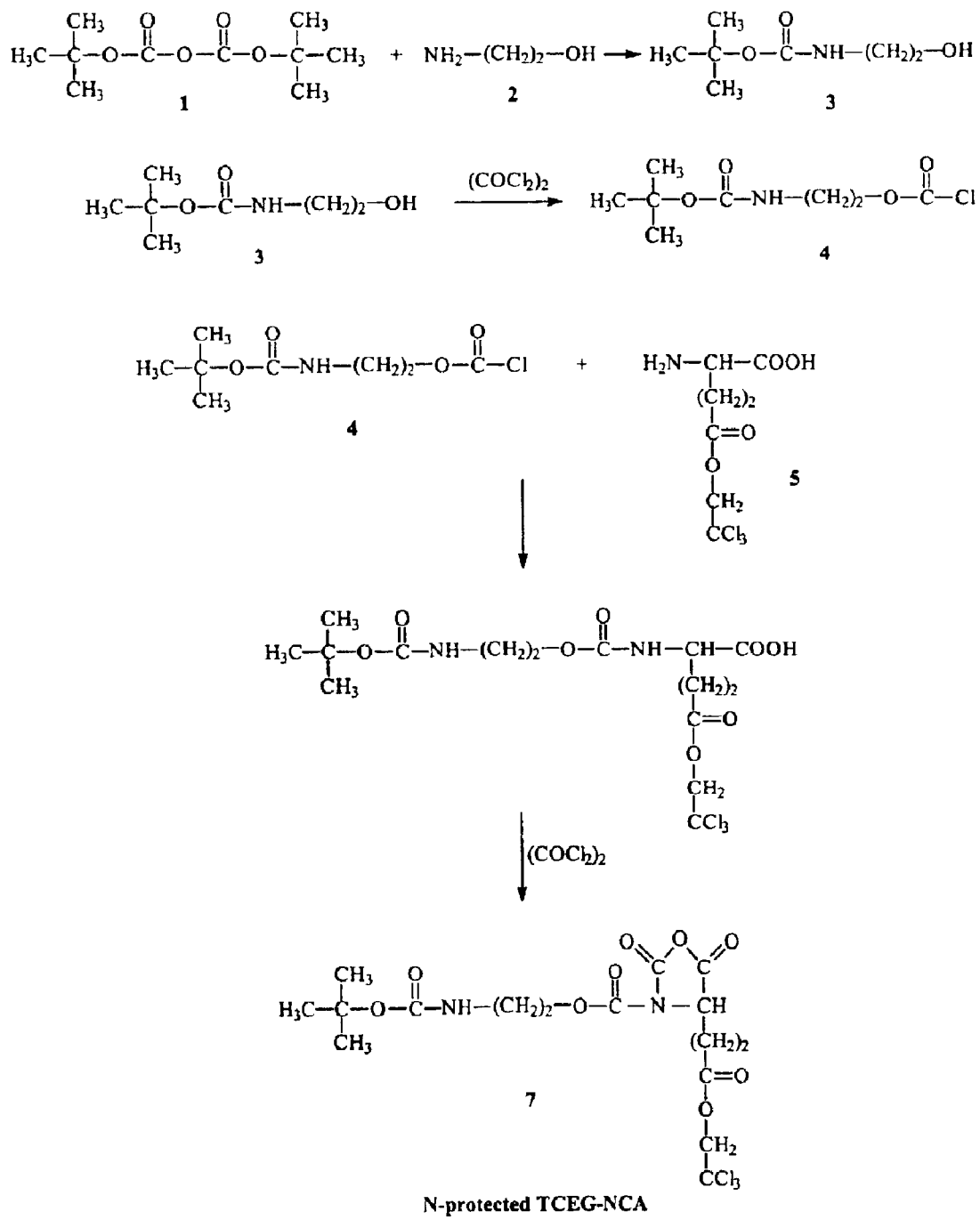
FIG. 1 is a schematic representation of an activated monomer process for making the linear poly-α-amino-acid derivatives of the invention.
Figure 2:
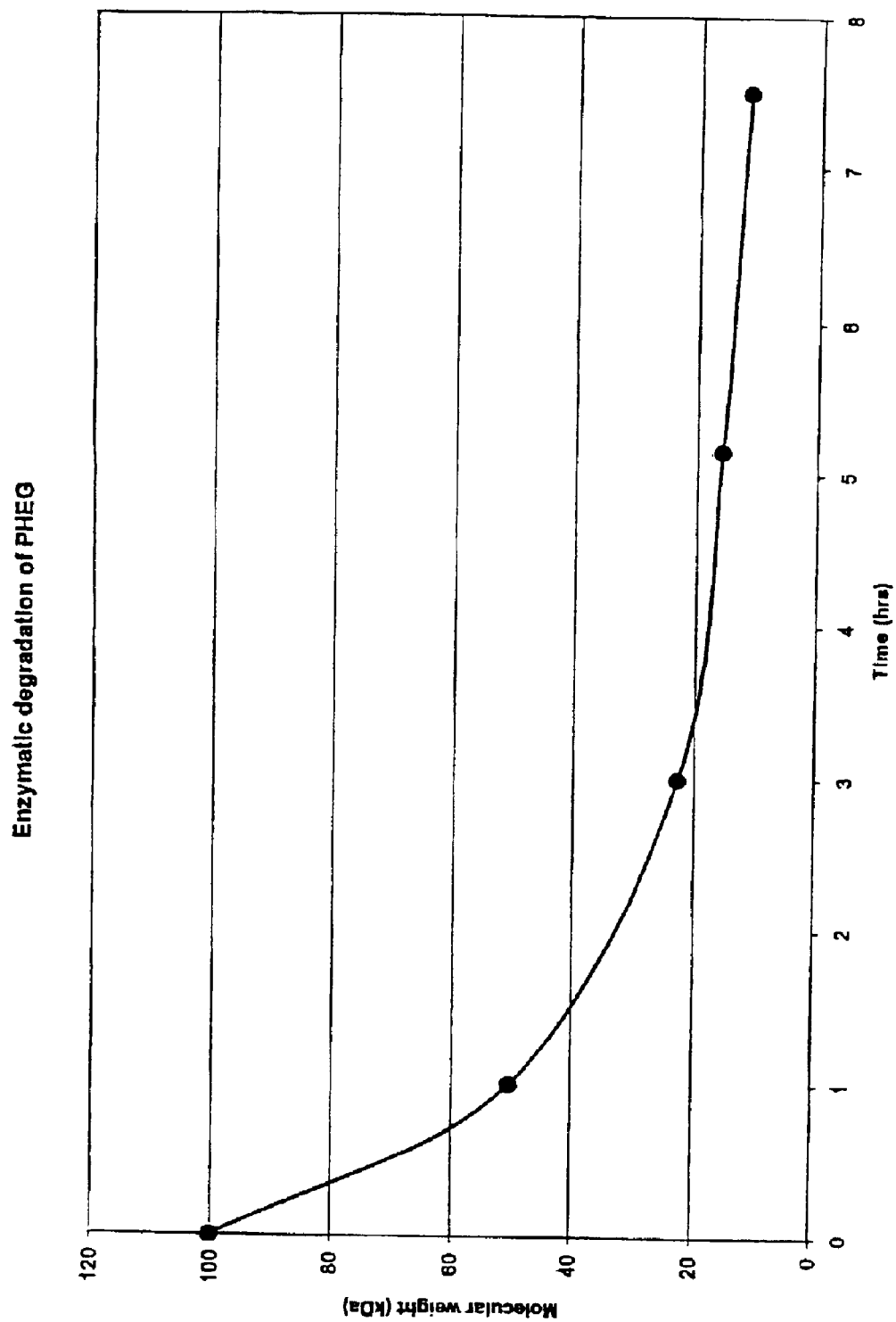
FIG. 2 is a representation of the biodegradation properties of poly[N-(2-hydroxyethyl)-L-glutamine](hereinafter referred as PHEG).

In a first embodiment, the present invention relates to novel poly-α-amino-acid derivatives having a functional (i.e. reactive) group at one or both ends of the polymer backbone and/or only a single functional group as a side group on the polymer backbone, the said functional end group and/or side group being other than alcohol. Specifically, this embodiment relates to linear poly-α-amino-acid derivatives having at least glutamic or aspartic or serinic repeating units and additionally having a functional (i.e. reactive) group at one or both ends of the polymer backbone and/or only a single functional (i.e. reactive) group as a side group on the said polymer backbone, the said functional end group and/or side group being other than alcohol. The reason for providing a single functional group when pending as a side-group on the polymer backbone is the ability to obtain a very precise coupling of the poly-α-amino-acid derivative of the invention with specific proteins. The said functional (i.e. reactive) end group and/or side group may be any reactive group, other than alcohol, that may be attached to either end of and/or be pending on the backbone of the said poly-α-amino-acid derivative containing at least glutamic or aspartic or serinic repeating units. In particular, it may be selected from the following functional groups: amine, carboxyl, ester, carbonate, thiol, thiol precursor (such as a disulfide), thioisocyanate, thiocarbonate, urea, thiourea, aldehyde, acetal, N-carboxyanhydride, oxycarbonyl (including carbonate ester, 2-oxycarbonyl pyridine, 2-oxycarbonyloxypyridine, succinimido carbonate, N-oxycarbonyl imidazole and the like), maleimide or any vinyl group suitable for radical, anionic or cationic polymerization such as styryl, acrylate, methacrylate, acrylamide, methacrylamide, vinyl ether, propenyl ether and the like. The terms "glutamic", "aspartic" and "serinic" as used herein, unless otherwise stated, are intended to mean the α-amino-acid sequence derived from glutamic acid or aspartic acid or serine respectively or, when available, from any ester or amide of such acids. More specifically, this embodiment relates to linear polymers having a number of repeating units of the formula:

$$—CO—CHR—NH—\quad (I)$$

wherein:
R is defined as $—(CH_2)_n—CO—OR_1$ or $—(CH_2)_N—CO—NHR_2$ or $CH_2OH$,
n is 1 or 2,
$R_1$ is selected from hydrogen, $C_{1-20}$ alkyl, polyhalo$C_{1-6}$alkyl, aryl$C_{1-6}$alkyl and heteroaryl$C_{1-6}$alkyl, and
$R_2$ is $C_{1-6}$alkyl substituted with at least one alcohol group, and further having a functional (i.e. reactive) group, such as above mentioned, at one or both ends of the polymer backbone and/or a single side group on the polymer backbone.

As will be detailed hereinafter, the novel poly-α-amino-acid derivatives of this invention are not limited to homopolymers comprising the said glutamic or aspartic or serinic repeating units, but they also include copolymers additionally comprising repeating units of one or more co-monomer(s) (hereinafter referred as A in the following formulae) copolymerizable with the α-amino-acid sequence derived from glutamic acid or aspartic acid or serine (such as hereinabove defined, i.e. including esters and amides thereof, when available). Non-limiting examples of such co-monomer repeating units include for instance any of the 17 naturally occuring α-amino-acids other than glutamic acid, aspartic acid and serine (in such case giving rise to either random or block copolymers) as well as polymer blocks or sequences derived from ethylene oxide or propylene oxide or mixtures thereof or from polyhydroxyalkanoates. Examples of the latter polymer sequences comprise for instance polymers and copolymers (whether random, block, segmented or grafted) of lactones such as ε-caprolactone, glycolide, L-lactide, D-lactide, meso-lactide, 1,4-dioxan-2-one, trimethylene carbonate (1,3-dioxan-2-one), γ-butyrolactone, δ-valerolactone, 1,5-dioxepan-2-one, 1,4-dioxepan-2-one, 3-methyl-1,4-dioxan-2,5-dione, 3,3 diethyl-1,4-dioxan-2,5-one, ε-decalactone, pivalolactone and 4,4-dimethyl-1,3-dioxan-2-one and the like. Several embodiments of such copolymers have been described by, among others, U.S. Pat. No. 5,951,997, U.S. Pat. No. 5,854,383 and U.S. Pat. No. 5,703,200 and shall therefore be considered as being within the scope of the present invention.

In the above definitions of groups included namely in formula (I) of the repeating units, and in other parts of the present specification, unless otherwise stated, the terms used shall have the following meanings:
halo is generic to fluoro, chloro, bromo and iodo;
$C_{1-6}$alkyl defines straight and branched chain saturated hydrocarbon radicals having from 1 to 6 carbon atoms such as, for example, methyl, ethyl, propyl, n-butyl, 1-methylethyl, 2-methylpropyl, dimethylethyl, 2-methylbutyl, n-pentyl, dimethylpropyl, n-hexyl, 2-methylpentyl, 3-methylpentyl and the like;
$C_{1-20}$ alkyl is meant to include $C_{1-6}$ alkyl (such as above defined) and the higher homologues thereof having 7 to 20 carbon atoms, such as for instance n-heptyl, 2-ethylhexyl, n-octyl, n-decyl, n-dodecyl, n-hexadecyl, n-octadecyl and the like;
polyhalo$C_{1-6}$alkyl is defined as polyhalosubstituted $C_{1-6}$alkyl, in particular $C_{1-6}$alkyl substituted with up to 8 halogen atoms such as difluoromethyl, trichloroethyl, trifluoromethyl, octafluoropentyl and the like;
aryl is defined as a mono- or polyaromatic group, such as phenyl, optionally substituted with one to three substituents each independently selected from $C_{1-6}$alkyl, nitro, cyano, halo and the like;
heteroaryl is defined as mono- and polyheteroaromatic groups, i.e. containing delocalized π electrons, such as those including one or more heteroatoms, namely 1-hetero-2,4-cyclopentadienyl, azabenzenyl and fused-ring derivatives thereof, in particular pyrrolyl, imidazolyl, pyrazolyl, triazolyl, tetrazolyl, furanyl, thienyl, oxazolyl, isoxazolyl, thiazolyl, isothiazolyl, oxadiazolyl, pyridinyl, pyrimidinyl, pyrazinyl, pyranyl, pyridazinyl, triazinyl, tetrazinyl, benzothienyl, isobenzothienyl, benzofuranyl, isobenzofuranyl, benzothiazolyl, benzoxazolyl, indolyl, isoindolyl, purinyl, pyrazolopyrimidinyl, benzimidazolyl, quinolyl, isoquinolyl, cinnolinyl, phtalazinyl, quinazolinyl, quinoxalinyl, thiazolopyridinyl, oxazolopyridinyl and imidazothiazolyl, including all possible isomeric forms thereof, wherein each of said heteroaromatic groups may optionally be substituted with one or, where possible, two or three substituents each independently selected from $C_{1-4}$ alkyl (as, for instance, in N-alkyl-2,5- dialkylpyrrolyl, 2,5-dialkylfuranyl and 2,5-dialkylthienyl), $C_{1-4}$ alkyloxy, $C_{1-4}$ alkylcarbonyl, hydroxy, nitro, halo and cyano;
$C_{3-7}$ cycloalkyl is generic to cyclopropyl, cyclobutyl, cyclopentyl, cyclohexyl and cycloheptyl;
When the α-amino-acid sequence of the poly-α-amino-acid derivative of this invention is a L-amino-acid sequence, the resulting polymer will be subject for enzymatic degradation and may conveniently be used for any purpose in biomaterial technology where polyethyleneglycol was previously used, including the chemical modification of biomolecules. On the other hand, when the α-amino-acid sequence of the poly-α-amino-acid derivative of this invention is a D-amino-acid sequence, the resulting polymer will be stable towards peptide degrading enzymes and may conveniently be used for the permanent surface modification of biomaterials.

As a general rule, the novel multifunctional (i.e. having at least two reactive groups, such as above defined, at the ends and/or on the side of the backbone) poly-α-amino-acid derivatives of the present invention may be described by any of the following formulae:

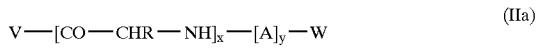 (IIa)

 (IIb)

 (IIb)

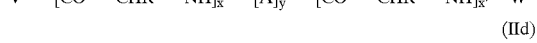 (IId)

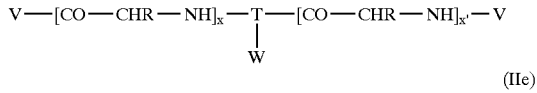 (IIe)

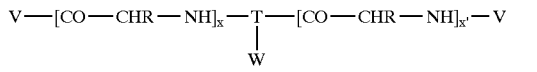

wherein:
R is as defined in formula (I),
x or, where applicable, x+x' range from 2 to about 2,000, preferably from 4 to about 500,
each of V and W independently represent a functional (i.e. reactive) group, able to be attached to an end or on the side of the polymer backbone containing the repeating units of formula (I),
A is at least a co-monomer co-polymerizable with the α-amino-acid sequence containing glutamic or aspartic or serinic repeating units,
y ranges from 0 to about 500, preferably from 0 to about 100,
T is a spacing unit selected from lysine and ornithine, and
V' is a non-reactive end group.

In the above definition, "non-reactive end group" should be understood as meaning a chemical group which cannot be used for coupling with proteins. Non-limiting examples of such non-reactive end groups include $C_{1-20}$ alkyl, oxy$C_{1-20}$alkyl, aryl, aryl$C_{1-20}$alkyl, amide, heteroaryl and heteroaryl$C_{1-20}$alkyl.

For instance as previously mentioned, A may be represented by the formula

—CO—CHR'—NH— (III)

wherein R' is the side-chain group of an α-amino-acid other than glutamic acid or aspartic acid or serine. For example R' may be the side-chain group of any of the other 17 well known naturally occuring α-amino-acids, i.e. lysine, arginine, histidine, glycine, asparagine, glutamine, cysteine, threonine, tyrosine, alanine, valine, leucine, isoleucine, proline, phenylalanine, methionine and tryptophan.

In another mode of implementation of the invention, A may be represented by the formula

—CH$_2$—CHR''—X'— (IV)

wherein:
R'' is selected from hydrogen and methyl, and
X' is selected from a single bond and oxygen,
i.e. [A], may be polyethylene glycol, polypropylene glycol and any copolymer of ethylene oxide and propylene oxide.

In still another mode of implementation of the invention, A may be at least a repeating unit derived from a hydroxy-alkanoate such as D or L lactic acid, glycolic acid, ε-caprolactone and the like. For instance, coupling of an amino-terminated poly-α-amino-acid derivative of this invention with a polyhydroxyalkanoate (based on one or more of the above-cited repeating units) having one or two hydroxyl end groups, e.g. in the presence of carbonyldiimidazole, leads to amphiphilic di-block or tri-block copolymers which, if properly designed by those skilled in the art, are able to form micelles in an aqueous medium and can thus be suitably used as a drug delivery system, namely in order to store hydrophobic drugs in the resulting micelles.

Similarly, the novel monofunctional (i.e. having a single reactive group at one end or on the side of the polymer backbone) poly-α-amino-acid derivatives of the present invention may be described by any of the following formulae:

 (Va)

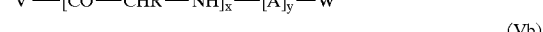 (Vb)

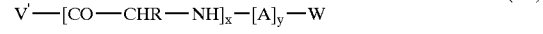 (Vc)

 (Vd)

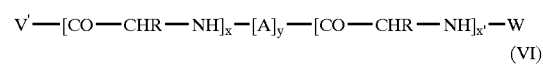 (VI)

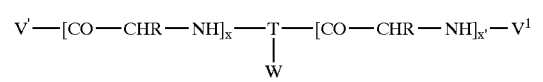

wherein:
R, x, x', A, y, T, V, V' and W are as defined in formulae (IIa) to (IIe), and
W' is a non-reactive end group such as above defined in respect of V'.

A first preferred class of novel poly-α-amino-acid derivatives according to the invention is a class of derivatives with at least one protective end group, being represented by the following formulae:

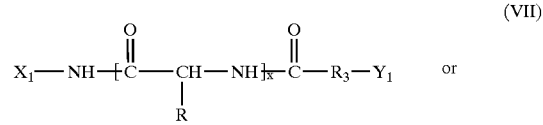 (VII)

or

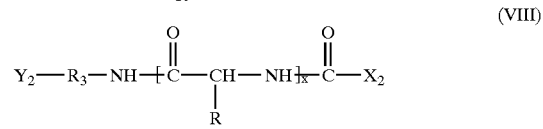 (VIII)

wherein:
R is —(CH$_2$)$_n$—CO—NHR$_2$,
R$_2$ and n are as defined in formula (I),
x is as defined in formulae (IIa) to (IIe),
X$_1$ is —R$_4$—Z$_1$—A$_1$,
each of R$_3$ and R$_4$ is independently selected from (CH$_2$)$_m$, arylene, C$_{1-6}$ alkylarylene and arylC$_{1-6}$alkylene,
m is from 2 to 20,
Y$_1$ is —Z$_2$—A$_2$, X$_2$ is —R$_4$—Z$_3$—A$_3$ or —O—R$_4$—Z$_3$—A$_3$,
Y$_2$ is —Z$_4$—A$_4$,
each of Z$_1$, Z$_2$, Z$_3$ and Z$_4$ is independently selected from NH, O, S, C(O)O, C(S)O, CO, CS, —OCH—O— and C=N—r$_5$, each of $A_1$, $A_2$, $A_3$ and $A_4$ is a protective group suitable for $Z_1$, $Z_2$, $Z_3$ and $z_4$ respectively, and $R_5$ is selected from hydrogen, $C_{1-6}$alkyl, aryl and $C_{1-6}$alkylaryl, heteroaryl and $C_{1-6}$alkylheteroaryl.

Protective groups $A_1$, $A_2$, $A_3$ and $A_4$ suitable for protecting $Z_1$, $Z_2$, $Z_3$ and $Z_4$, i.e. NH, O, S, CO, CS and C=N—$R_5$ are well known to those skilled in the art of organic and peptide chemistry. An illustrative but non-limiting example of a group suitable for protecting the amino group NH is e.g. —C(O)—O—$CH_2$—$C_6H_5$. Illustrative but non-limiting examples of groups suitable for protecting the sulfur atom include triphenylmethyl, 2-thiopyridyl and acyloxymethyl. Illustrative but non-limiting examples of a group suitable for protecting groups like CO, CS and C=N—$R_5$or the oxygen atom are e.g. tetrahydropyranyl, tert-butyl and the like.

Another preferred class of novel polyα-amino-acid derivatives according to the invention, which may serve namely as intermediate compounds for preparing the derivatives of formula (VII), is represented by the following formula:

X$_1$—NH—[CO—CHR—NH]$_x$—CO—CHR—NH$_2$ (IX)

wherein:

$X_1$ is as defined in formula (VII), x is as defined in any of formulae (IIa) to (IIe), R is defined as —(CH$_2$)$_n$—CO—OR$_1$, and $R_1$ and n are as defined in formula (I).

Another preferred class of novel poly-α-amino-acid derivatives according to the invention, which may serve namely as intermediate compounds, is represented by formula (VIII) wherein R is defined as being

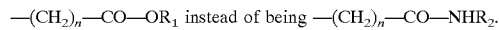

—(CH$_2$)$_n$—CO—OR$_1$ instead of being —(CH$_2$)$_n$—CO—NHR$_2$.

Another preferred class of derivatives has reactive end groups that can be covalently coupled with a functional group selected from amine, alcohol, thiol, carboxylic acid, disulfide and maleimide, or that contain polymerizable end groups. They may be represented by the formulae, respectively (X) and (XI):

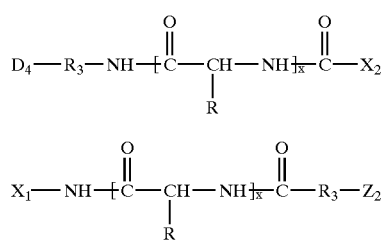

wherein:

R is —(CH$_2$)$_n$—CO—NHR$_2$, $R_2$ and n are as defined in formula (I), x is as defined in any of formulae (IIa) to (IIe), $X_1$ is —$R_4$—$Z_1$—$D_1$, each of $R_3$ and $R_4$ is independently selected from (CH$_2$)$_m$, arylene, $C_{1-6}$ alkylarylene and aryl$C_{1-6}$alkylene, m is from 2 to 20, each of $R_3$—$Y_1$ and $R_3$—$Y_2$ may be a group including a vinyl terminal moiety such as for instance ethylidenyl or styryl, $X_2$ is —$R_4$—$Z_3$—$D_3$, each of $Z_1$, $Z_2$, $Z_3$ and $Z_4$ is independently selected from NH, O, S, C(O)O, C(S)O, CO, CS, —OCH—O— and C=N—$R_5$, each of $D_1$, $D_2$, $D_3$ and $D_4$ is independently selected from hydrogen, aryl, heteroaryl, succinimidyl, vinyl, $C_{1-6}$alkylcarbonyl, each of $Z_1$—$D_1$, $Z_2$—$D_2$, $Z_3$—$D_3$ and $Z_4$—$D_4$ may be independently selected from maleimidyl, disulfide, α-haloacetoxy and $C_{,1-6}$alkyloxymethylsulfide, and $R_5$ is selected from hydrogen, $C_{1-6}$alkyl, aryl and $C_{1-6}$alkylaryl, heteroaryl and $C_{1-6}$alkylheteroaryl.

Preferably in the above class of reactive derivatives (X) and (XI), D, should be different from $D_2$, and $D_3$ should be different from $D_4$, otherwise some degree of crosslinking cannot be excluded.

Yet another class of novel poly-α-amino-acid derivatives according to the invention is a class of derivatives with only a single reactive side group other than alcohol on the polymer backbone. Another preferred class of novel poly-α-amino-acid derivatives according to the invention is a class of derivatives with two reactive groups at both ends of the polymer backbone and additionally with only a single reactive side group on the polymer backbone, the said reactive groups being other than alcohol.

In a second embodiment, the present invention relates to processes for obtaining the novel monofunctional and heterobifunctional poly-α-amino-acid derivatives described hereinabove (the term "heterobifunctional" here should be understood as referring to derivatives having the above formulae and wherein the functional groups V and W are different from each other). As a general procedure, such processes include a step comprising polymerizing a monomer or mixture of monomers comprising at least the N-carboxy-anhydride of an amino-acid selected from glutamic acid, aspartic acid, serine and oxygen-protected serine in the presence of an effective amount of a multifunctional initiator containing at least one primary amino group and further containing at least another functional group selected from maleimide, thioisocyanate, thiocarbonate, urea, thiourea, aldehyde, acetal, oxycarbonyl, vinyl (such as acrylate, methacrylate, acrylamide, methacrylamide and the like), ester, carbonate, thiol precursor, protected amine and protected carboxylic acid and/or in the presence of an effective amount of a bi-functional terminating reagent. The terms "oxygen-protected serine", "protected amine" and "protected carboxylic acid" as used herein are well understood from those skilled in the art of peptide chemistry. Illustrative and non-limiting examples of most common multifunctional initiators include amino-acid esters, α-amino-ω-di$C_{1-6}$alkylacetals, α,α'-diamino $C_{1-6}$alkytdisulfides and α-amino-ω-maleimido alkanoic acid amides. Initiation using a multifunctional initiator and termination by adding a monofunctional terminating reagent as well as initiation using a monofunctional initiator and termination by adding a bifunctional terminating reagent leads to derivatives with one single functional (i.e. reactive) group at one end of the linear polymer backbone. A combination of multifunctional initiation and bifunctional termination reactions provides a polymer with functional (i.e. reactive) groups at both ends of the linear polymer backbone.

Initiation by a diamine having a protected carboxyl group, such as the terbutylester or the ω-amino alkylacyl derivatives of lysine or ornithine, leads to a poly-α-amino-acid derivative having a single pendant protected carboxyl side group. If the terminating reagent is monofunctional, then the chain ends will be non reactive. If the terminating reagent is heterobifunctional, then the chain ends will be reactive. If no terminating reagent is used, then the polymer backbone will have amino end groups.

If during the polymerization of the N-carboxy anhydride of glutamic acid, aspartic acid, serine or oxygen-protected serine, termination would occur by formation of a pyrrolidone end group, then this process will only be applicable for preparing derivatives having one single functional group. However, in such event, heterofunctional derivatives can still be prepared by the alternative so-called "activated monomer process" described below and schematically represented in FIG. 1.

Non limiting examples of multifunctional initiators which can be used in the process of the invention are:

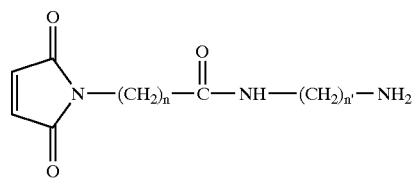

(XII)

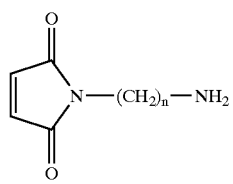

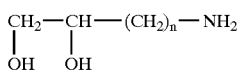

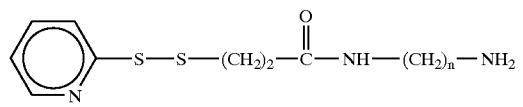

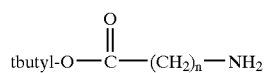

(XIII)

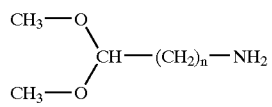

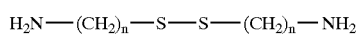

The initiator having the formula (XII), which may be obtained by reacting a commercially available compound represented by the formula (XIV) hereunder with a diamine $H_2N-(CH_2)_n-NH_2$, is believed to be a novel organic reagent, as well as the initiator having the formula (XIII) which may be obtained by reacting monotritylamine with N-succinimidyl 3(2-pyridyldithio) propionate.

Non limiting examples of terminating reagents which can be used in the process of the present invention are:

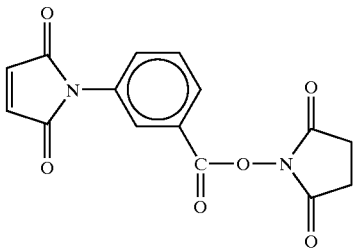

(XIV)

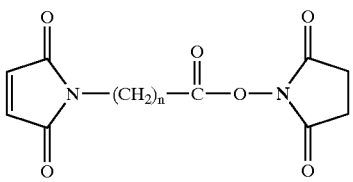

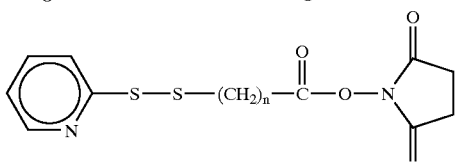

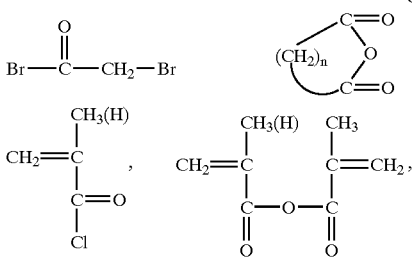

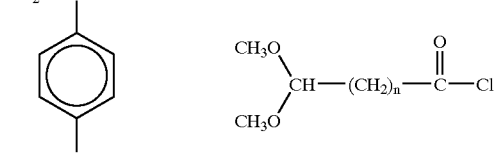

Illustrative but non-limiting examples of the principal monomers suitable for performing the above-mentioned polymerization step of the process of the present invention include the N-carboxy-anhydrides of γ-methyl, γ-benzyl and γ-trichloroethyl glutamates and the N-carboxy-anhydrides of β-methyl, β-benzyl and β-trichloroethyl aspartates. As previously indicated, the process of the invention may involve the copolymerisation of a comonomer such as the N-carboxy-anhydride of another α-amino acid.

The polymerization step of the process of this invention preferably takes place in the presence of a solvent for the above-described monomers, especially the N-carboxy-anhydride of glutamic acid, aspartic acid, serine or oxygen-protected serine. Examples of such solvents are preferably aprotic solvents including chlorinated hydrocarbons such as 1,2-dichloroethane, amides such as dimethylformamide, N-methylpyrrolidone or dimethylacetamide. dimethylsulfoxide, esters such as ethyl acetate and the like. Depending on the nature of the solvent selected, the polymerization temperature may range from about 0° C. to about 100° C., preferably from 10 to 30° C. Polymerization is usually effected for a period of time of about 0,5 to 72 hours, preferably from 1 to 24 hours, depending on the targeted molecular weight The amount of the multifunctional initiator containing at least one primary amino group to be used in the polymerization step of the process of the invention preferably ranges between about 0.2 and 30 mole % with respect to the N-carboxy-anhydride monomer. The amount of the bi-functional terminating reagent to be used in the polymerization step of the process of the invention preferably ranges between about 2 and 5 equivalents with respect to the molar amount of the multifunctional initiator used.

Following the polymerization step, the process of the invention may include aminolysis of the pending $R_1$ group of the repeating unit of formula (I) by means of an effective amount of an amino-alcohol, such as for instance 2-aminoethanol or 2,3-dihydroxy-propylamine, in the presence of an effective amount of an activating agent or reaction promoter such as for instance 2-hydroxypyridine, N,N-dimethylaminopyridine, N-methylimidazole and the like. An effective amount of the amino-alcohol to be used during the said aminolysis step usually ranges from about 1 to 50, preferably 1 to 5, equivalents with respect to the monomeric units in the polymer formed in the previous polymerization step. An effective amount of the activating agent or reaction promoter to be used during the said aminolysis step usually ranges from about 0.5 to 5 equivalents with respect to the monomeric units in the polymer formed in the previous polymerization step. The aminolysis step of the process of this invention preferably takes place in the presence of a solvent for the polymer derived from the N-carboxy-anhydride of glutamic acid, aspartic acid, serine or oxygen-protected serine. Examples of suitable solvents for this aminolysis step are namely aprotic solvents including amides such as dimethylformamide, N-methylpyrrolidone or dimethylacetamide, dimethylsulfoxide, esters such as ethyl acetate and the like.

For instance, the synthesis of poly[$N^5$-(2-hydroxy-ethyl)-L-glutamine] (PHEG) may be performed by first polymerizing the N-carboxy-anhydride of γ-benzyl-L-glutamate or γ-trichloroethyl-L-glutamate, followed by aminolysis of the resulting poly-γbenzyl-L-glutamate or poly-γ-trichloroethyl-L-glutamate using a large excess of 2-aminoethanol in presence of 2-hydroxypyridine.

This first route for obtaining the novel functional poly-αamino-acid derivatives of the invention without termination due to the formation of a pyrrolidone end group may be represented by the sequence of chemical reactions shown in FIG. 1 and now explained in further details:

a) polymerization step:

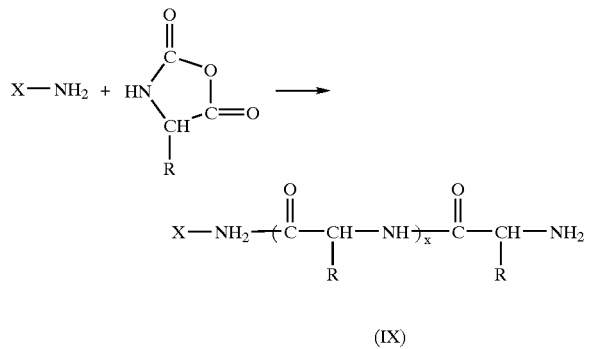

(IX)

b) end-group functionalization step
This step proceeds through reaction of the compound of formula (IX) with a reactive ester or anhydride having the formula $Y_1$—$R_3$—$COOR_6$, wherein $R_6$ is a reactive ester or anhydride.

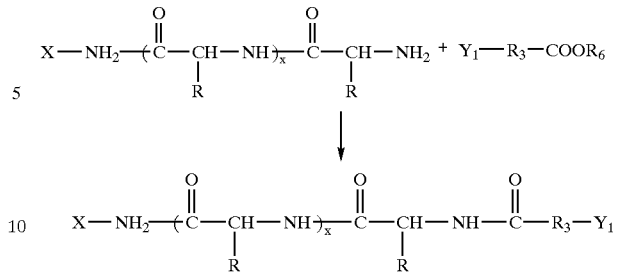

c) aminolysis step:

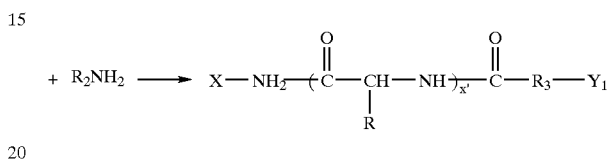

wherein R is —$(CH_2)_n$—CO—$NHR_2$.

Mono- and bifunctional poly α-amino-acid derivatives according to the invention may also alternatively be prepared by the so-called "activated monomer mechanism" of polymerization of N-carboxy anhydrides as schematically represented on FIG. 1:

a) preparation of a suitable N-carboxy anhydride mixture from the α-aminoacid.

In this first step, part of the relevant α-amino-acid (for instance glutamic acid, aspartic acid or serine) is N-acylated, for instance by means of an haloformate or carbonyl halide having the formula $X_2COX$ wherein X is a halogen atom such as chlorine and $X_2$ is as defined in formula (VIII), then both the N-acylated α-amino-acid and the remaining part of the same α-amino-acid are separately treated, for instance by means of phosgene or diphosgene, in order to form both N-carboxy anhydrides shown below. Non limiting examples of haloformates which can suitably be used for this first step are:

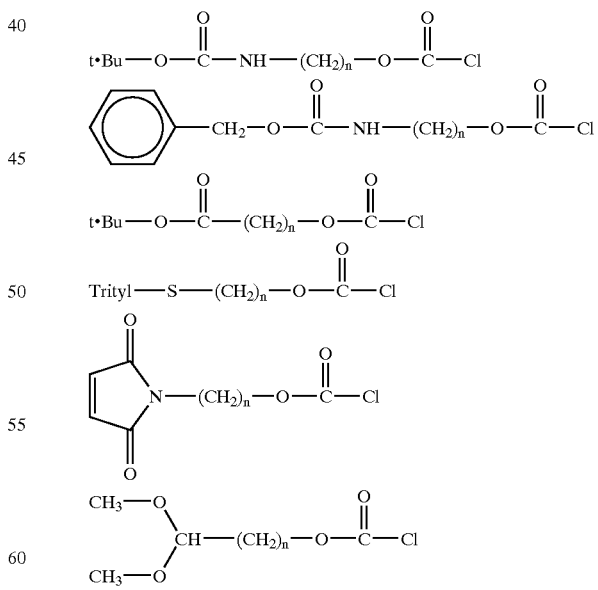

Non limiting examples of carbonyl halides which can suitably be used for this first step are compounds having formulae similar to the above haloformate formulae but where the —O—C(O)—Cl terminal group is replaced by a —C(O)—Cl terminal group.

b) ring-opening copolymerization and explicit chain growth mechanism.

In this second step, a mixture of the N-carboxy anhydrides obtained in the first step is copolymerized in the presence of an excess of an initiator such as a tertiary amine (e.g. tributylamine). The N-carboxy anhydride of the α-amino acid is preferably used in a controlled excess with respect to the N-carboxy anhydride of the N-acylated α-amino-acid, their ratio determining the final molecular weight.

c) end-group modification of polymer.

In this third step, the N-carboxy anhydride-terminated polymer obtained in the second step is reacted with a reagent having the formula $H_2N$—$R_3$—$Y_2$, wherein $R_3$ and $Y_2$ are as defined in formula (VIII). If the said terminating reagent $H_2N$—$R_3$—$Y_2$ is a diamine containing a protected carboxyl group, then the said termination reaction will lead to a poly-α-amino-acid derivative having one single protected carboxyl side group.

Non-limiting examples of functionalized amines suitable for use in this step of the second process of the invention may be taken for instance from the list of multifunctional initiators provided hereinbefore in relation with the first process of the invention.

d) aminolysis step

As shown hereinbelow, this step proceeds essentially as in the first route of obtention previously described.

As an example, a heterobifunctional derivative of the invention can be prepared via this second procedure by polymerization of γ-benzyl-L-glutamate or the N-carboxyanhydride of γ-trichloroethyl-L-glutamate (TCEG-NCA) (in excess) with N-acylated TCEG-NCA and using tributylamine as an initiator, followed by termination with a compound containing a functional amino end group (or a diamine having a protected carboxylic group) and another functional end group, and subsequent aminolysis of the trichloroethylester side groups with ethanolamine.

In a third embodiment, the present invention relates to biodegradable articles containing a copolymer comprising at least a moiety derived from a poly-α-amino-acid derivative such as above described, particularly one having any of the formulae (IIa), (IIb), (IIc), (IId), (IIe), (Va), (Vb), (Vc), (Vd), (VI), (VII) and (VIII), provided that the functional group at one or both ends thereof—i.e. V and/or W in formulae (IIa), (IIb), (IIc), (IId), (IIe), (Va), (Vb), (Vc), (Vd) and (VI), $R_3$—$Y_2$ and/or $R_3$—$Y_1$ in formulae (VII) and (VIII)—is an unsaturated group, and at least a moiety derived from an unsaturated comonomer copolymerizable therewith. The said unsaturated comonomer copolymerizable with the unsaturated poly-α-amino-acid derivative of the present invention may be for instance an β-olefin, an α,β-unsaturated monocarboxylic acid, ester, nitrile or amide (such as acrylic, methacrylic and the like), an unsaturated dicarboxylic acid anhydride (such as maleic anhydride) or any other vinyl terminated monomer (such as styrene, α-methylstyrene, vinyl ether, propenyl ether and the like) or any combination thereof. The respective proportions of the said unsaturated comonomer and of the said unsaturated poly-α-aminoacid derivative may easily be selected and adapted by those skilled in the art, depending on the reactivity ratio of the said comonomers and on the biodegradability level and kinetics to be achieved in the final biodegradable article, which may in addition comprise usual biodegradability additives.

In a fourth embodiment, the present invention relates to the use of a novel functional poly-α-amino acid derivative such as above described, particularly one having any of the formulae (IIa), (IIb), (IIc), (IId), (IIe), (Va), (Vb), (Vc), (Vd), (VI), (VII), (VIII) and (IX), for the modification of a biologically-active ingredient. This invention therefore also relates to any product resulting from such modification, including the product of coupling it with or grafting it onto the said biomolecule. As already indicated hereinabove, derivatives containing a L-amino-acid sequence, being enzymatically degradable, are most useful for this purpose. The biologically-active ingredient to be modified according to this invention, preferably to be used in a biologically effective amount, may be such as a therapeutic, diagnostic or prophylactic agent. The therapeutic agent or drug can be selected for its antimicrobial properties, capability for promoting repair or reconstruction of specific tissues or for specific indications. These include for instance antimicrobial agents such as broad spectrum antibiotics for combating clinical and sub-clinical infections, for example gentamycin, vancomycine and the like. Other therapeutic agents or drugs which can be considered for modification by means of the poly-α-aminoacid derivative of this invention are naturally occurring or synthetic organic or inorganic compounds well known in the art, including proteins and peptides (produced either by isolation from natural sources or recombinantly), hormones, carbohydrates, antineoplastic agents, antiangiogenic agents, vasoactive agents, anticoagulants, immunomodulators, cytotoxic agents, antiviral agents, antibodies, neurotransmitters, oligonucleotides, lipids, plasmids, DNA and the like. Therapeutically active proteins which can additionally be modified according to this invention include, without any specific limitation, fibroblast growth factors, epidermal growth factors, platelet-derived growth factors, macrophage-derived growth factors such as granulocyte macrophage colony stimulating factors, ciliary neurotrophic factors, cystic fibrosis regulator genes, tissue plasminogen activator, B cell stimulating factors, cartilage induction factor, differentiating factors, growth hormone releasing factors, human growth hormone, hepatocyte growth factors, immunoglobulins, insulin-like growth factors, interleukins, cytokines, interferons, tumor necrosis factors, nerve growth factors, endothelial growth factors, non-steroidal anti-inflammatory drugs, osteogenic factor extract, T cell growth factors, tumor growth inhibitors, enzymes (e.g. superoxide dismutase, asparaginase, ribonuclease, adenine deaminase, xanthine oxidase and the like), as well as fragments thereof. Other biomolecules which can also be modified in this way include human serum albumin, lysine, cysteine and the like.

Diagnostic agents which can be regarded as biologically-active ingredients to be modified according to this invention (and to be used preferably in an effective amount for performing the relevant diagnostic) indude, without any specific limitation, conventional imaging agents (for instance as used in tomography, fluoroscopy, magnetic resonance imaging and the like) such as transition metal chelates.

The novel functional poly-α-aminoacid derivatives of this invention are also useful for the modification of antibodies, and fragments thereof, having a thiol group and/or an amino group. More specifically, the present invention relates to antibodies modified by means of the said functional poly-α-aminoacid derivatives and having a second functionality for hooking and/or being able to attach another targeting group such as an antibody or a fragment thereof, an oligopeptide that is recognized by cell membrane integrines, such as the tripeptide RGD (arginin-glycine-aspartic acid), the tetrapeptide RGDS (meaning RGD-serine) or the like (as is well known to those skilled in the art, RGD is found in the integrin-binding domains of a number of ligands, and sequences flanking this tripeptide are presumed to determine the exact binding specificity), peptides (such as mellitin) which stimulate cell membrane penetration, transferin, saccharides and oligosaccharides such as galactose, mannose and the like.

As already indicated hereinabove, derivatives containing a D-aminoacid sequence are useful for the surface modification of biomaterials. Such modified surfaces may be obtained either by grafting poly-α-amino acid derivatives such as PHEG on the surface or by coating the surface with a PHEG-containing copolymer. As an example, poly-[N-(2-hydroxyethyl)-L-glutamine] having an unsaturated end group (such as styryl, acrylate, acrylamide, methacrylate, methacrylamide and the like) can be adsorbed from a solution containing Eosin Y and triethanolamine onto a material surface. Subsequent light irradiation results in polymerization of the unsaturated end groups. Via the same procedure, comonomers and crosslinking agents such as a bismethacrylate can also be co-adsorbed and copolymerized. Another method of using poly-[N-(2-hydroxyethyl)-L-glutamine] having an unsaturated end group consist of copolymerizing it with a comonomer and to apply the resulting copolymer from solution onto a substrate. Yet another method consist of generating reactive groups (such as carboxylic acid or anhydride) onto a material surface and then to make them react with a suitable PHEG-end group (e.g. an amino end group).

The novel functional poly-α-amino acid derivatives of this invention are also useful for the building-up and/or the modification of a synthetic vector component, for instance for gene delivery, such as polyethyleneimine (either branched or linear), poly-L-lysine, a star-shaped dendrimer (e.g. of the polypropyleneimine type or the polyamidoamine type) or chitosan. Thus the present invention contributes to solve the problem of efficient delivery to target cells in vivo. At present viruses provide the most popular vectors for in vivo delivery, particularly with improved DNA packaging techniques. However, their inherent immunogenicity, possibility of fixing complement, poor target selectivity and difficulty of scale-up production, together with concerns over potential toxicity, seem likely to prevent their widespread acceptance. There is therefore a need for alternative safe and efficient DNA or gene delivery systems preferably based on fully synthetic carrier vehicles. A synthetic carrier vehicle or vector suitable for efficient targeted delivery of DNA or other nucleic acid material in vivo must fulfil various biological requirements. Ideally it would be stable in the blood circulation, non-immunogenic and resistant to enzymatic degradation, capable of efficient target-discrimination, and able to penetrate the target cell membrane selectively to gain access to the nucleus, release the nucleic acid and enable efficient transcription within the target cell. For successful and versatile in vivo application it is very important that nucleic acid delivery vehicles should be small enough to gain access to target cells.

Therefore another embodiment of the present invention is a synthetic polymer for a polymer-based carrier vehicle or vector for delivery of DNA or other nucleic acid material to target cells in a biological system, comprising a linear poly-α-amino-acid derivative such as above described. In particular the said polymer may be one having any of formulae (IIa), (IIb), (IIc), (IId), (IIe), (Va), (Vb), (Vc), (Vd), (VI), (VII), (VIII) and (IX). The nucleic acid material may include for instance genomic DNA, DNA fragments of any length, plasmid DNA, cDNA, RNA, oligonucleotides, DNA expression vectors, RNA, ribozymes and the like. Antisense nucleic acid may also be used for certain therapies. In the DNA carrier vehicles provided by this invention, the DNA expression vector usually is a plasmid-based expression vector incorporating an appropriate promoter sequence.

Yet another embodiment of the present invention is a method of treatment of a patient (i.e. a mammal, preferably a human) in need of such treatment, comprising administration to said patient of a biologically-active ingredient (such as above disclosed) modified by or a nucleic acid material carried by a polymer system comprising a linear poly-α-amino-acid derivative such as disclosed above in details. For instance, the invention provides a method of delivering gene DNA material to a patient in carrying out somatic gene therapy treatment, said method comprising packaging the selected DNA as a expression vector in a carrier vehicle constructed as herein described, and administering the polyelectrolyte complex material forming the DNA carrier vehicle to said patient.

EXAMPLE 1—polymerisation of N-carboxyanhydride of γ-trichloroethyl-L-glutamate.

2 g of N-Carboxyanhydride of γ-trichloroethyl-L-glutamate (TCEG-NCA, obtained for instance from glutamic acid, trichloroethanol and phosgene) is dissolved in 20 ml dry 1,2-dichloroethane and the resulting solution is cooled down to 10° C. 1-Triphenylmethylaminoethylamine (0,099 g, i.e. 5 mole % with respect to TCEG-NCA) is dissolved in 2 ml 1,2-dichloroethane and added to the solution of TCEG-NCA. Polymerisation of TCEG-NCA is then effected by maintaining the temperature at 10° C. After two hours, polymerisation is determined to be complete by infrared spectroscopy, then a three-fold molar excess of acetic anhydride and equimolar quantity of triethylamine are added and the reaction mixture is stirred for another two hours at room temperature. The solution is precipitated in pentane and the polymer produced is isolated by filtration and dried under vacuum. Its molecular weight is determined by $^1$H NMR (DMF-d$_7$) and gel permeation chromatography (polystyrene standard, tetrahydrofuran as eluent) to be $M_n$=6,000. $^1$H NMR (DMF-d$_7$) analysis confirms the following structure of the polymer:

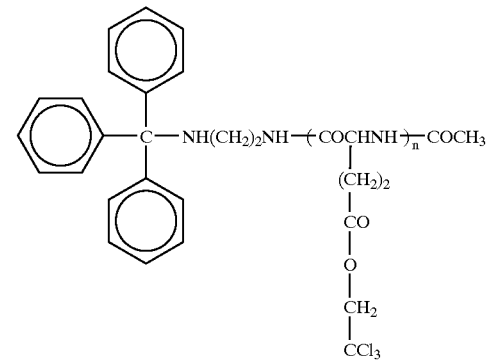

EXAMPLE 2—aminolysis of the trichloroethylester of poly-L-glutamic acid.

1 g (3,8 mmole) of the polymer obtained in example 1 is dissolved in 10 ml dry N,N-dimethylformamide. This solution is cooled down to 10° C. and 0,69 ml (11,5 mmole) ethanolamine and 0,36 g (3,8 mmole) 2-hydroxypyridine are then added. The reaction is followed by infrared spectroscopy and, after two hours, determined to be complete (100% conversion). The resulting aminolysed polymer is isolated by precipitation in ether, filtrated, dried under vacuum and then purified by gel filtration on Sephadex G-25 (water as eluent) and isolated by lyophilization. The purified polymer is characterised by $^1$H NMR (D$_2$O) and gel permeation chromatography (dextran standards, water as eluent) as having a molecular weight $M_n$ of 4,000. $^1$H NMR analysis confirms the following structure for this polymer:

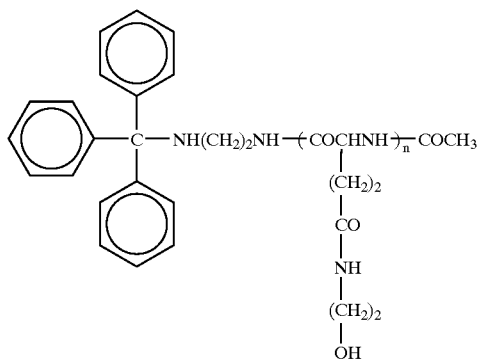

EXAMPLE 3—deprotection of poly-[-N-(2-hydroxyethl)-L-glutamine] (PHEG)

1 g of the polymer of example 2 is dissolved in 10 ml trifluoroacetic acid and stirred at room temperature for half an hour. Trifluoroacetic acid is then removed by evaporation under vacuum. The resulting polymer is dissolved In water and centrifugated, then the supernatant is purified by gel filtration on Sephadex G-25 (water as eluent) and isolated by lyophilization. $^1$H NMR (D$_2$O/DCl) analysis confirms the following structure of the polymer:

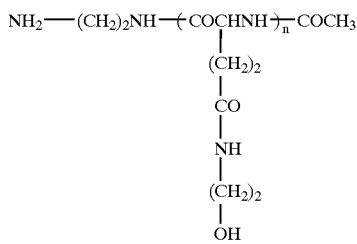

EXAMPLE 4—functionalization of poly-[N-(2-hydroxyethyl)-L-glutamine] by means of disulfide groups.

1 g of the polymer of example 3 is dissolved in 0,1 M phosphate buffer, pH 7,5 (100 ml). 0.6 g N-succinimidyl 3-(2-pyridyidithio) propionate (SPDP) is dissolved in 30 ml ethanol and added to the polymer solution. After two hours reaction at room temperature, the mixture is separated on Sephadex G-25 (water as eluent) and the resulting functional polymer (PHEG-SPDP) is isolated by lyophilization. $^1$H NMR (D$_2$O) analysis confirms the following structure of the polymer:

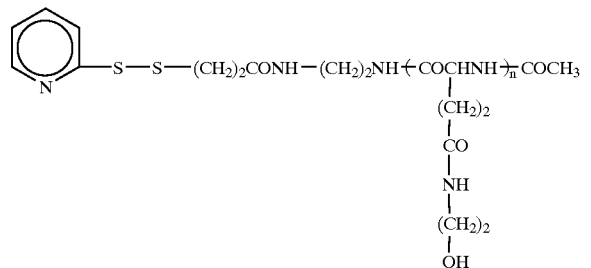

The concentration of pyridyidithio groups is determined also in the presence of 0.1 M dithiothreitol (hereinafter referred to as DTT), using $\epsilon = 8080$ M$^{-1}$cm$^{-1}$ at 343 nm for released pyridine-2-thione.

EXAMPLE 5—functionalization of poly-[N-(2-hydroxyethyl)-L-glutamine] by means of thiol end group.

The functional polymer of example 4 (PHEG-SPDP) is dissolved in 0,1 M acetate buffer, pH 4,5, containing 0,1 M NaCl (10 mg/ml), and DTT is added to provide a concentration of 10 mM. After 30 minutes at room temperature, the DTT-treated mixture is desalted into 0.1 M sodium phosphate buffer (pH 7.2) containing 1 mM ethylenediaminotetraacetic acid (EDTA). The number of thiol groups generated is determined by means of 5,5'-dithiobis(2-nitrobenzoic acid).

EXAMPLE 6—functionalization of poly-[N-(2-hydroxyethl)-L-glutamine] by means of maleimide end group.

1 g of the polymer of example 3 is dissolved in 0,1 M phosphate buffer, pH 7.0 (200 ml). Maleimidobenzoyl-N-hydroxysuccinimide ester (0.2 g) is dissolved in 10 ml N,N-dimethylformamide and added to the polymer solution. After stirring at room temperature for 1 hour, the mixture is separated on Sephadex G-25 (water as eluent) and the resulting functional polymer is isolated by lyophilization. $^1$H NMR (D$_2$O) analysis confirms the following structure of the polymer:

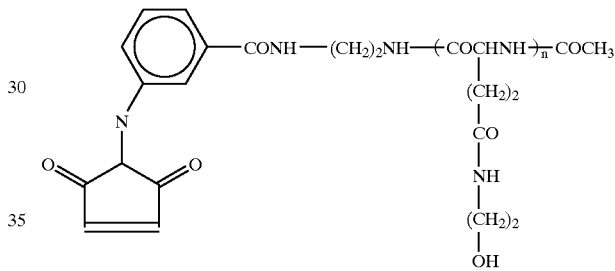

EXAMPLE 7—polymerisation of N-carboxyanhydride of γ-trichloroethyl-L-glutamate.

The preparation, isolation and characterisation procedures of example 1 are repeated, except that polymerisation is initiated by 0.017 g aminoacetaldehyde-dimethylacetal (5 mole %). $^1$H NMR (DMF-d$_7$) confirms the following structure of the polymer obtained:

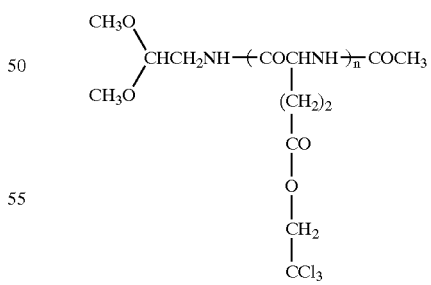

EXAMPLE 8—aminolysis of trichloroethyl ester of poly-L-glutaimic acid.

The aminolysis of the polymer of example 7 is carried out while using the procedure as described in example 2. $^1$H NMR (D$_2$O) confirms the following structure of the polymer obtained:

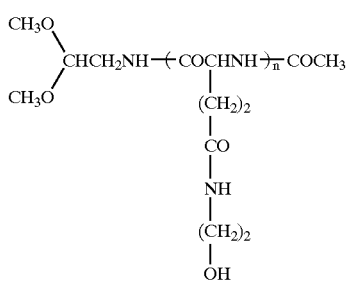

EXAMPLE 9—preparation of a poly-[N-(2-hydroxyethyl)-L-glutamine] with aldehyde end group.

1 g of the functional polymer of example 8 is dissolved in 10 ml hydrochloric acid (3%) and stirred at room temperature for one hour, then the mixture is separated on Sephadex G-25 and the polymer obtained is isolated by lyophilizabon. $^1$H NMR (D$_2$O) and determination of the aldehyde groups by reaction with hydroxylamine hydrochloride confirm the following structure of the polymer obtained:

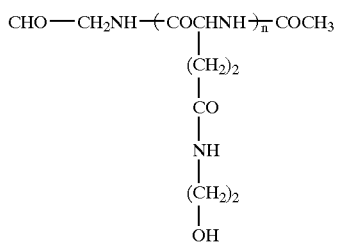

EXAMPLE 10—polymerisation of N-carboxyanhydride of γ-trichloroethyl-L-glutamate.

TCEG-NCA (2 g) is dissolved in 20 ml dry 1,2dichloroethane and the solution is cooled down to 10° C. 2-Methbxyethylamine (0,023 g, i.e. 5 mole % with respect to TCEG-NCA) is dissolved in 2 ml 1,2-dichloroethane and added to the previous solution. After two hours, polymerisation is determined by infrared spectroscopy to be complete, then a three-fold molar excess of methacrylic anhydride and equimolar quantity of triethylamine are added and the reaction mixture is stirred for another two hours at room temperature. The solution is precipitated in pentane and the polymer is isolated by filtration and dried under vacuum. The molecular weight is determined by $^1$H NMR (DMF-d$_7$) and gel permeation chromatography (polystyrene standard, tetrahydrofuran as eluent) to be 6,500. $^1$H NMR (DMF-d$_7$) analysis confirms the following structure of the polymer:

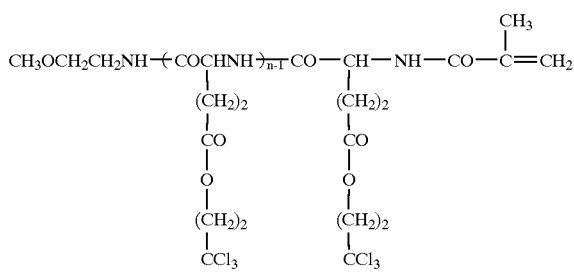

EXAMPLE 11—aminolysis of trichlomethyl ester of poly-L-glutamic acid

The aminolysis of the polymer of example 10 is carried out while using the procedure as described in example 2. $^1$H NMR (D$_2$O) confirms the following structure of the polymer obtained:

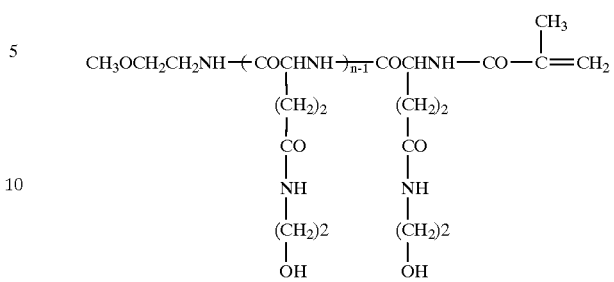

EXAMPLE 12—polymerisation of N-carboxyanhydride of γ-trichloroethyl-L-glutamate.

TCEG-NCA (2 g) is dissolved in 20 ml dry 1,2-dichloroethane, then the solution is cooled down to 10° C. 2-Methoxyethylamine (0,023 g, 5 mole % with respect to TCEG-NCA) is dissolved in 1,2-dichloroethane (2 ml) and added to the previous solution. After two hours, polymerisation is determined by infrared spectroscopy to be complete, then a three-fold molar excess of succinic anhydride and equimolar quantity of triethylamine are added and the reaction mixture is stirred for 24 hours at room temperature. Then 1.2 g citric acid is dissolved in 50 ml water and added to the reaction mixture. The resulting polymer is extracted with 1,2-dichloroethane, the solution is dried over MgSO$_4$ and precipitated in pentane. The polymer is isolated by filtration and dried under vacuum. $^1$H NMR (DMF-d$_7$) confirms the following structure of the polymer obtained:

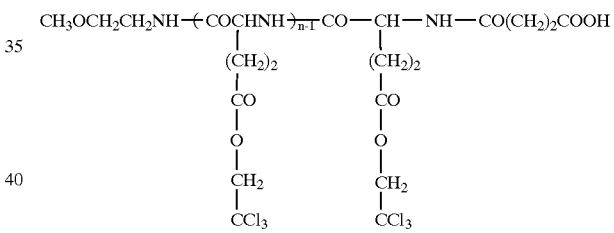

EXAMPLE 13—aminolysis of trichloroethyl ester of poly-L-glutamic acid

The aminolysis of the polymer of example 12 is carried out while using the procedure as described in example 2. $^1$H NMR (D$_2$O) confirms the following structure of the polymer obtained:

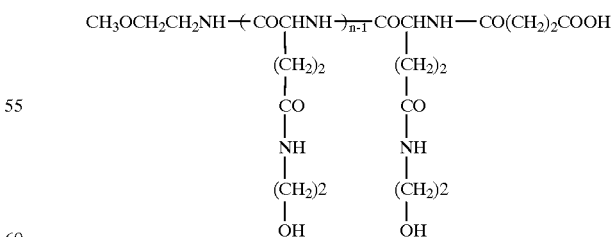

EXAMPLE 14—preparation of poly-[N-(3-hydroxypropyl)-L-glutamine] with functional end groups.

Polymerisation of TCEG-NCA is first initiated by means of suitable initiators or terminated by means of suitable terminating agents as described in examples 1, 6 and 7. Then aminolysis of such polymers is carried out as described in example 2, except that ethanolamine is replaced with 3amino-1-propanol. After deprotection (as in example 3) or hydrolysis (as in example 9), functional polymers having the following structures were obtained:

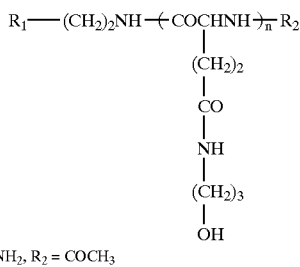

R₁ = NH₂, R₂ = COCH₃
R₁ = SS-Py, R₂ = COCH₃
R₁ = maleimide, R₂ = COCH₃
R₁ = CHO, R₂ = COCH₃
R₁ = CH₃O, R₂ = CH=CH₂
          |
          CH₃
R₁ = CH₃O, R₂ = COOH

EXAMPLE 15—preparation of poly-[N-(2,3-dihydroxypropyl)-L-glutamine] with functional end groups.

Polymerisation of TCEG-NCA is first initiated by means of suitable initiators or terminated by means of suitable terminating agents as described in examples 1, 6 and 7. Then aminolysis of such polymers is carried out as described in example 2, except that ethanolamine is replaced with 3-amino-1,2-propanediol. After deprotection (as in example 3) or hydrolysis (as in example 9), functional polymers having the following structures were obtained:

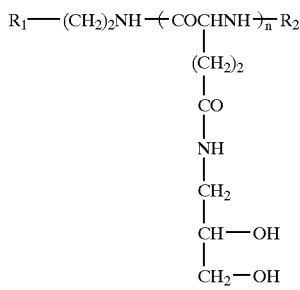

R₁ = NH₂, R₂ = COCH₃
R₁ = SS-Py, R₂ = COCH₃
R₁ = maleimide, R₂ = COCH₃
R₁ = CHO, R₂ = COCH₃
R₁ = CH₃O, R₂ = CH=CH₂
          |
          CH₃
R₁ = CH₃O, R₂ = COOH

EXAMPLE 16—polmerisation of N-carboxynhydride of γ-trichloroethyl-L-aspartate.

N-Carboxyanhydride of γ-trichloroethyl-L-aspartate (TCEA-NCA) (2 g) is dissolved in 20 ml dry 1,2-dichloroethane, then the solution is cooled down to 10° C. 1-Triphenylmethylaminoethylamine (0,0999, i.e. 5 mole % with respect to TCEA-NCA) is dissolved in 1,2-dichloroethane (2 ml) and added to the previous solution. After two hours, polymerisation is determined by infrared spectroscopy to be complete, then a three-fold molar excess of acetic anhydride and equimolar quantity of triethylamine are added and the reaction mixture is stirred for another two hours at room temperature. The solution is then precipitated in pentane and the resulting polymer is isolated by filtration and dried under vacuum. The molecular weight is determined by $^1$H NMR (DMF-$d_7$) and gel permeation chromatography (polystyrene standard, tetrahydrofuran as eluent) to be $M_n$=5,000. $^1$H NMR (DMF-$d_7$) analysis confirms the following structure of the polymer:

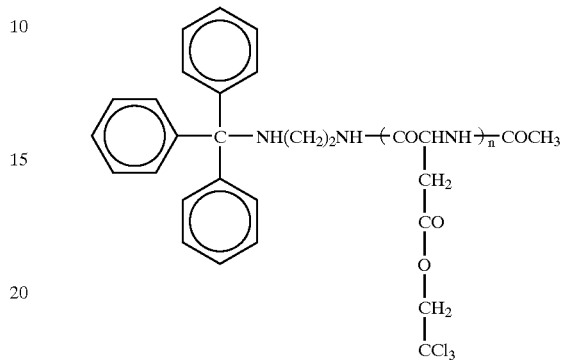

EXAMPLE 17—aminolysis of trichloroethyl ester of poly-L-aspartic acid.

1 g (3,8 mmole) of the polymer of example 16 is dissolved in 10 ml dry N,N-dimethylformamide. This solution is cooled down to 10° C., then 0,69 ml (11,5 mmole) ethanolamine and 0,36 g (3,8 mmole) 2-hydroxypyridine are added. The reaction is followed by infrared spectroscopy and, after two hours, determined to be complete (100% conversion). The resulting aminolyzed polymer is isolated by precipitation in ether, filtrated and dried under vacuum and then purified by gel filtration on Sephadex G-25 (water as eluent) and isolated by lyophilization. The purified polymer is characterised by $^1$H NMR ($D_2O$) and gel permeation chromatography (dextran standard, water as eluent) as having a molecular weight $M_n$ of 3,500. $^1$H NMR analysis confirms the following structure of the polymer:

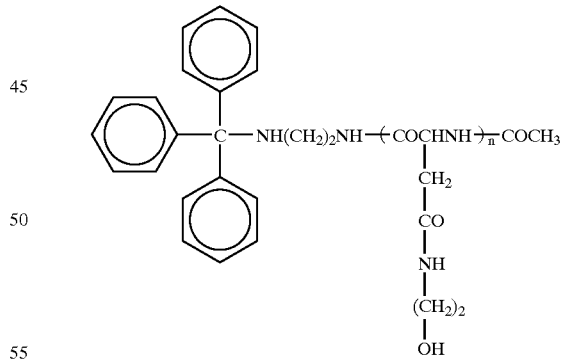

EXAMPLE 18—deprotection of poly-[N-(2-hydroxyethyl)-L-aspartate]

1 g of the polymer of example 17 is dissolved in 10 ml trifluoroacetic acid and stirred at room temperature for half an hour. Trifluoroacetic acid is removed by evaporation under vacuum. The polymer is dissolved in water and centrifugated, then the supernatant is purified by gel filtration on Sephadex G-25 (water as eluent) and isolated by lyophilization. $^1$H NMR ($D_2O$/DCl) analysis confirms the following structure of the polymer:

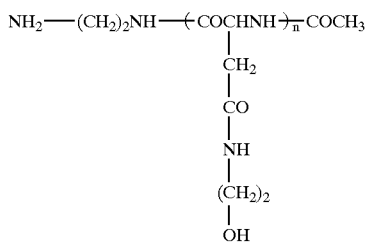

EXAMPLE 19—coupling of an aldehyde-terminated PHEG with human serum albumin.

The aldehyde-terminated poly-[N-(2-hydroxyethyl)-L-glutamine] (PHEG) of example 9 in a 0,1 M sodium acetate buffer(10 mg/ml) at pH 4.0 is added to a solution of human serum albumin (hereinafter referred to as HAS) in the same buffer (10 mg/ml). After 16 hours at room temperature, the resulting product is purified by gel filtration chromatography on Sephadex G-50 equilibrated with phosphate buffer saline (hereinafter referred to as PBS). Fractions containing purified 1:1 PHEG-CH=N-HSA conjugates are pooled, concentrated by precipitation with ammonium sulfate, dissolved into PBS, and stored at 4° C. When coupling was carried out in the presence of a reducing agent, e.g. sodium cyanoborohydride, a more stable conjugate PHEG-CH$_2$NH-HSA was obtained.

EXAMPLE 20—coupling of a disulfide-terminated PHEG with human serum albumin.

First, thiolation of HSA is effected according to the following procedure: to HSA (10 mg/ml) in PBS is added a five-fold excess of SPDP dissolved in a minimal amount of dimethylformamide. After stirring at room temperature for 30 minutes, the solution is desalted into 0,1 M acetate buffer (pH 4.5) containing 0,1 M NaCl and dithiothreitol (DTT) is added to give a concentration of 10 mM. After 20 minutes at room temperature, the DTT-treated mixture is desalted into 0,1 M sodium phosphate buffer (pH 7,2) containing 1 mM ethylenediaminotetraacetic acid (EDTA). The number of thiol groups generated is determined by means of 5,5'-dithiobis(2-nitrobenzoic acid).

Then thiolated HSA is reacted with a disulfide-terminated PHEG as follows: the polymer of example 4 in 0,1 M sodium phosphate buffer (pH 7.2) containing 1 mM EDTA (10 mg/ml) is mixed with thiolated HSA in the same buffer to provide a 4:1 HAS/PHEG molar ratio. After stirring at room temperature for 16 hours, the conjugate obtained is purified by gel filtration chromatography on Sephadex G-50 equilibrated with PBS. Fractions containing purified 1:1 HSA-SS-PHEG conjugates are pooled, concentrated by precipitation with ammonium sulfate, dissolved into PBS, and stored at 4° C. The same conjugate can also be prepared by reacting the functional PHEG of example 5 with HAS modified by SPDP at similar conditions.

EXAMPLE 21—coupling of a maleimide-terminated PHEG with human serum albumin.

First, thiolation of HSA is carried out as described in example 20. Then thiolated HSA is reacted with a maleimide-terminated PHEG as follows: for the preparation of a conjugate with a thioether bond, the polymer of example 6 in 0,1 M sodium phosphate buffer (pH 7.2) containing 1 mM EDTA (10 mg/ml) is mixed with thiolated HSA in the same buffer in order to provide a 4:1 HAS/PHEG molar ratio. After stirring at room temperature for 16 hours, the conjugate obtained is purified by gel filtration chromatography on Sephadex G-50 equilibrated with PBS. Fractions containing purified 1:1 HSA-S-PHEG conjugates are pooled, concentrated by precipitation with ammonium sulfate, dissolved into PBS, and stored at 4° C.

EXAMPLE 22—biodegradation of poly[N-(2-hydroxyethyl)-L-glutamines]

10 mg of a poly[N-(2-hydroxyethyl-L-glutamine] (PHEG) produced according to example 3, except that its molecular weight $M_n$ is 102,000 is dissolved in 1,2 ml phosphate-citrate buffer (pH 5.5) containing 0,2% (weight/volume) Triton X-100. 200 µl EDTA (10 ml in buffer), 200 µl reduced glutathion (50 ml in buffer) and 400 µl tritosomes (2,5 mg/ml in buffer) are added. These mixtures are incubated at 37° C. Samples are taken at predetermined periods of time and analysed by gel permeation chromatography (dextran standard, phosphate-citrate buffer pH 6.0 as eluent) for their avrage number molecular weight. The table hereunder, as well as FIG. 1, clearly demonstrate the biodegradability of PHEG by means of the decreasing molecular weight.

| Time (hrs) | Molecular weight |
|---|---|
| 0 | 100,000 |
| 1 | 50,270 |
| 3 | 22,660 |
| 5.16 | 15,920 |
| 7.5 | 11,700 |

EXAMPLE 23—coupling of an aldehyde-terminated PHEG with enzyme superoxide dismutase The aldehyde-terminated poly-[N-(2-hydroxyethyl)-L-glutamine] (PHEG) of example 9 in 0,1 M phosphate buffer (10 mg/ml), pH 5.5, is added to a solution of superoxide dismutase (hereinafter referred to as SOD) in the same buffer (10 mg/ml). After 4 hours at room temperature a reducing agent, e.g. sodium cyanoborohydrate, is added and a stable conjugate, PHEG-CH$_2$NH-SOD is obtained. The product is purified by using an Amicon ultrafiltration system with a PM-10 membrane and lyophilized. The degree of substitution (defined as the proportion of amino groups in SOD which are coupled), determined by the 2,4,6-trinitrobenzenesulfonic acid (hereinafter referred as TNBS) method, is 50 mole %.

EXAMPLE 24—coupling of a carboxylic-terminated PHEG with enzyme superoxide dismutase PHEG with carboxylic end group from example 13 is dissolved in 0.1 M phosphate buffer (10 mg/ml), pH 7.4. 1-Ethyl-3-(dimethylaminopropyl) carbodiimide hydrochloride (1 equivalent) is added. Superoxide dismutase (SOD) is dissolved in the same buffer (10 mg/ml) and added to the above solution. After 1 hour at room temperature the product is purified as in example 23 and lyophilized. The degree of substitution, determined by TNBS method, is 40 mole %.

EXAMPLE 25—coupling of an aldehyde-terminated PHEG with polyethyleneimine

The aldehyde-terminated poly-[N-(2-hydroxyethyl)-L-glutamine] (PHEG) of example 9 in 0,1 M phosphate buffer (10 mg/ml), pH 5.5, is added to a solution of polyethyleneimine (hereinafter referred to as PEI) in the same buffer (10 mg/ml). After 2 hours at room temperature the product is reduced by means of sodium cyanoborohydrate and a stable conjugate, PEI-g-PHEG, is obtained. The product is purified as in example 23 and lyophilized. The degree of substitution, determined by using $^1$H NMR spectroscopy and TNBS method, is 20 mole %. Similar conjugates can be prepared by coupling the said aldehyde-terminated PHEG with poly-L-lysine or another cationic polymer containing primary amino groups in its side chains.

EXAMPLE 26—coupling of a carboxylic-terminated PHEG with poly-L-lysine

PHEG with carboxylic end group from example 13 is dissolved in 0.1 M phosphate buffer (10 mg/ml), pH 7.4. 1 equivalent of 1-ethyl-3-(dimethylaminopropyl) carbodiimide hydrochloride is added. Poly-L-lysine (hereinafter referred to as PPL) is dissolved in the same buffer (10 mg/ml) and added to the above solution. After 2 hours at room temperature the conjugate obtained, PLL-g-PHEG, is purified as in example 23 and lyophilized. The degree of substitution, determined by $^1$H NMR spectroscopy and TNBS method, is 20 mole %.

EXAMPLE 27—Synthesis of N-acylated N-carboxyanhydride of γ-trichloroethyl-L-glutamate This synthesis procedure is presented in the scheme shown below and comprises the following steps:
a) synthesis of terbutoxycarbonyl aminoethanol:
A solution of 2.1 ml ethanolamine (10 mmole) in a mixture of dioxane (20 ml), water (10 ml) and 1 N NaOH (10 ml) is cooled in an ice-water bath. 2.4 g Di-tert-butyl dicarbonate (11 mmole) is added with stirring and the reaction proceeds for ½ hour. The solution is concentrated under vacuum, cooled in an ice-water bath, covered with a layer of ethyl acetate (30 ml) and acidified with a dilute solution of KHSO$_4$ to pH 2–3. The aqueous phase is extracted with ethyl acetate. The ethyl acetate extracts are dried over anhydrous MgSO$_4$ and evaporated under vacuum, yielding 95% terbutoxycarbonyl aminoethanol, the structure of which is confirmed by $^1$H NMR (CDCl$_3$) analysis.
b) synthesis of terbutoxycarbonylaminoethyl chlorocarbonate:
A solution of 1 g diphosgene (5 mmole) in dichloromethane (5 ml) is cooled in an ice-water bath and a solution of 1.02 g terbutoxycarbonyl aminoethanol (5 mmole, prepared in step a) in dichloromethane (10 ml) is added in small portions under stirring. Stirring is continued for about 2 hours. The solvent and excess of phosgene are removed under vacuum and the product is purified by recrystallization from ether, yielding 96% terbutoxycarbonylaminoethyl chlorocarbonate, the structure of which is confirmed by $^1$H NMR (CDCl$_3$) analysis.
c) synthesis of terbutoxycarbonylaminoethyloxycarbonyl-N-γ-trichloroethyl-L-glutamate
2.63 g γ-Trichloroethyl ester of L-glutamic acid (10 mmole) is dissolved in tetrahydrofuran (150 ml) under slight heating and then cooled to 15° C. The solution is treated with 21 g of an aqueous solution of sodium bicarbonate (25 mmole) and 3.16 g terbutoxycarbonylaminoethyl chlorocarbonate (12 mmole) under vigorous stirring. Stirring is continued for about 3 hours. The solution is extracted with ether and acidified to pH 2–3 with hydrochloric acid. The solid product obtained is washed with water, dried over phosphorous pentoxide under vacuum and purified by recrystallization from ethyl acetate, yielding 94% terbutoxycarbonylaminoethyloxycarbonyl-N-γ-trichloroethyl-L-glutamate, the structure of which is confirmed by $^1$H NMR (CDCl$_3$) analysis.
d) synthesis of N-acylated N-carboxyanhydride of γ-trichloroethyl-L-glutamate
1 g N-acylated trichloroethyl monoester of L-glutamic acid (2 mmole) is dissolved in 30 ml tetrahydrofuran under stirring. 0.4 g diphosgene (2 mmole) is added in portions, the solution is stirred under reflux for 2 horrs and flashed with nitrogen gas under stirring for another 2 hours. The resulting product is precipitated in pentane, filtered and dried under vacuum, yielding 75% of N-acylated N-carboxyanhydride of γ-trichloroethyl-L-glutamate, the structure of which is confirmed by $^1$H NMR (CDCl$_3$) analysis.

EXAMPLE 28—polymerization of TCEG-NCA with N-acylated TCEG-NCA 2 g N-carboxyanhydride of γ-trichloroethyl-L-glutamate (TCEG-NCA) is dissolved in 20 ml dichloromethane. Solutions of the N-acylated TCEG-NCA (0.17 g, i.e. 5 mole % with respect to TCEG-NCA) in 5 ml dichloromethane and tributylamine (0.06 g, i.e. 5 mole % with respect to TCEG-NCA) in 2 ml dichloroethane are added to the solution of TCEG-NCA. After the end of the polymerization (about 3 hours), determined by infrared spectroscopy, a solution of 2-aminoethyl propionamide-3-maleimide (prepared from triphenylmethyl ethylamine and 6-maleimidocaproic acid and then deprotected with trifluoroacetic acid) (three-fold excess with respect to the initiator) in 5 ml dichloromethane and an equimolar amount of triethylamine are added and the reaction mixture is stirred for another 3 hours at room temperature. The solution is precipitated in pentane and the resulting polymer is isolated by filtration and dried under vacuum. Its molecular weight, determined by $^1$H NMR (DMF-d$_7$), is 6,000. $^1$H NMR (DMF-d$_7$) confirms the following structure of the polymer:

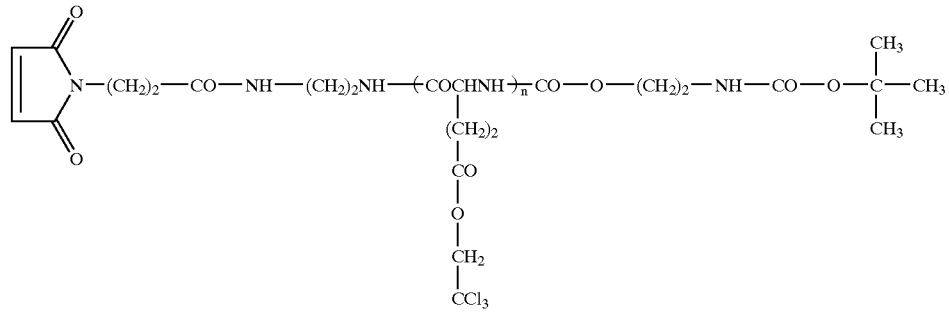

EXAMPLE 29—aminolysis of a poly-γ-trichloroethyl-L-glutamate containing a maleimido end group and a terbutoxycarbonyl N-acylated end group.

The aminolysis procedure is performed as in example 2, resulting in a polymer with a molecular weight, determined by $^1$H NMR (D$_2$O), of 4,000. $^1$H NMR (D$_2$O) confirms the following structure of the polymer:

pyridyidithio) propionate (SPDP) is added and the reaction mixture is stirred for another 2 hours at room temperature. The solution is precipitated in pentane and the resulting polymer is isolated by filtration and drying under vacuum. Its molecular weight, determined by $^1$H NMR (DMF-d$_7$) and GPC (polystyrene standards, THF as eluent) is M$_n$=6,000. $^1$H NMR (DMF-d$_7$) confirms the following structure of the polymer:

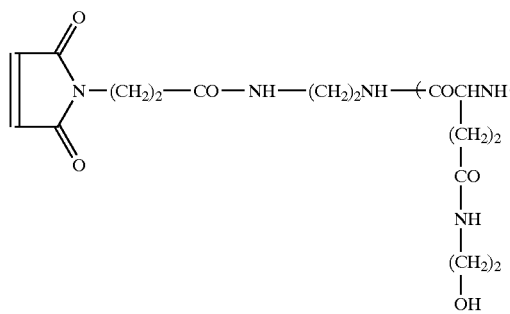

EXAMPLE 30—deprotection of a terbutoxycarbonyl group in a polymer.

1 g of the polymer of example 29 is dissolved in 10 ml trifluoroacetic acid and stirred at room temperature for 0,5 hour. Trifluoroacetic acid is removed by evaporation under vacuum. The resulting polymer is dissolved in water and centrigugated. The supernatant product is purified by gel filtration on Sephadex G-25 (water as eluent) and isolated by lyophilization. $^1$H NMR (D$_2$O) confirms the following structure of the polymer:

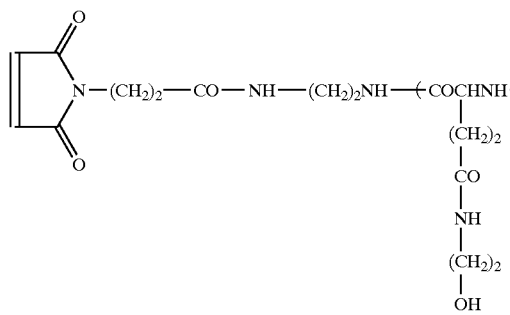

EXAMPLE 31—synthesis of a heterobifunctional PHEG.

a) polymerization of N-carboxyanhydride of γ-trichloroethyl-L-glutamate 2 g N-Carboxyanhydride of γ-trichloroethyl-L-glutamate (TCEG-NCA) is dissolved in 20 ml dry 1,2-dichloroethane. The solution is cooled down to 10° C. 0,099 g 1-triphenylmethylaminoethylamine (5 mole % with respect to TCEG-NCA) is dissolved in 2 ml 1,2-dichloroethane and added to the solution of NCA. After the end of the polymerisation, determined by infrared spectroscopy, a three-fold molar excess of N-succinimidyl 3-(2-

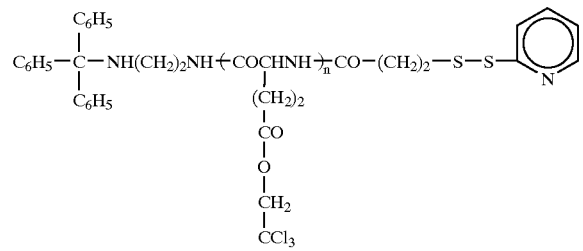

b) aminolysis of trichloroethyl ester of poly-L-glutamic acid 1 g (3,8 mmole) of the above polymer is dissolved in 10 ml dry N,N-dimethylformamide. The solution is cooled down to 10° C. and 0.69 ml (11,5 mmole) ethanolamine and 0.36 g (3,8 mmole) 2-hydroxypyridine are added. The reaction is followed by infrared spectroscopy. After the end of aminolysis, the resulting polymer is precipitated in ether, filtrated and dried under vacuum. It is then purified by gel filtration on Sephadex G-25 (water as eluent), isolated by lyophilization and characterised by $^1$H NMR (D$_2$O) and GPC (dextran standards, water as eluent) as having a molecular weight $M_n$=4,500. $^1$H NMR analysis confirms the following structure of the polymer:

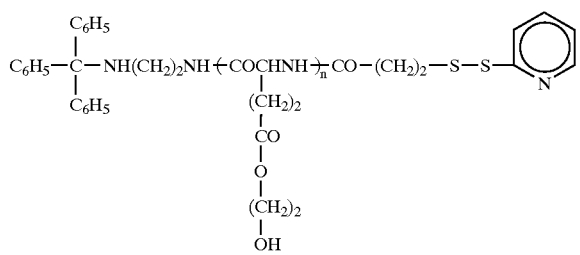

c) deprotection of triphenylmethyl group 1 g of the above polymer is dissolved in 10 ml trifluoroacetic acid and stirred at room temperature for 0,5 hour. Trifluoroacetic acid is removed by evaporation under vacuum. The resulting polymer is dissolved in water and centrigugated. The supernatant is purified by gel filtration on Sephadex G-25 (water as eluent) and isolated by lyophilization. $^1$H NMR (D$_2$O/DCl) analysis confirms the following structure of the polymer:

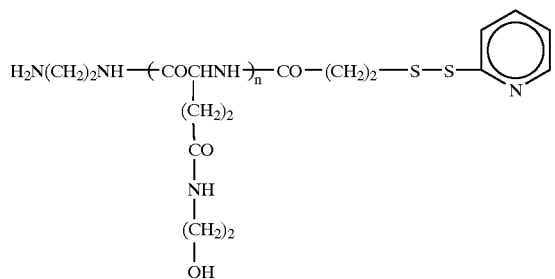

EXAMPLE 32—synthesis of a PHEG derivative terminated with a carboxyl group and a disulfide group 1 g of the polymer of step (c) of example 31 (0.22 mmole) is dissolved in 50 ml N,N-dimethylformamide. 0.024 g succinic anhydride (0.24 mmole) and an equimolar amount of dimethylaminopyridine are added and the solution is stirred for 1 hour. Then the solvent is removed under vacuum and the residue is dissolved in water. The unsoluble part is filtered off and the filtrate is purified by dialysis and lyophilized. $^1$H NMR (D$_2$O) analysis confirms the following structure of the polymer:

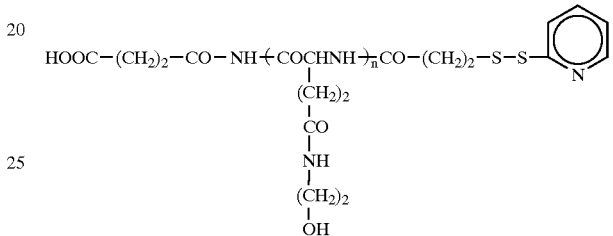

EXAMPLE 33—synthesis of PHEG terminated with an N-hydroxysuccinimide ester and a disulfide group 1 g of the polymer of example 32 (0.22 mmole) is dissolved in 30 ml N,N-dimethylformamide at 0° C. 0.05 g N-hydroxysuccinimide (0.44 mmole) is added under stirring followed by 0.09 g dicyclohexylcarbodiimide (0.44 mmole). The solution is left at room temperature and maintained under stirring for 4 hours, after which the precipitated dicyclohexylurea is removed by filtration. The solvent is removed under vacuum and the product is triturated with ether, filtered and dried under vacuum. $^1$H NMR (DMF-d$_7$) analysis confirms the following structure of the polymer:

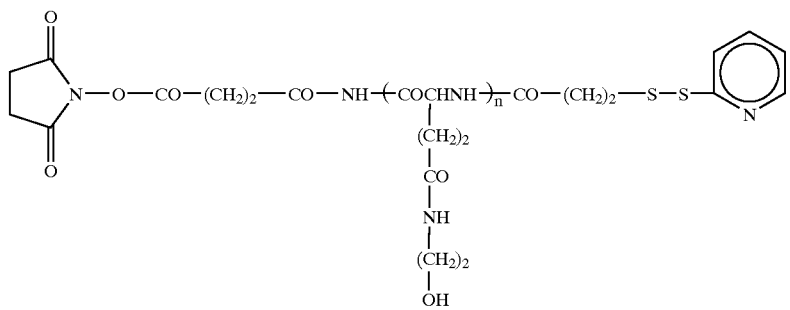

EXAMPLE 34—coupling of a hetero bifunctional PHEG with superoxide dismutase

The polymer of example 33 is dissolved in 0.02 M borate buffer, pH 8.0 (10 mg/ml) and added to a solution of superoxide dismutase (SOD) in the same buffer (10 mg/ml). The solution is left for 1 hour at room temperature. The resulting product is purified by using an Amicon ultrafiltration system with a PM-10 membrane and lyophilized. The degree of substitution, determined by TNBS, is 40%. A schematic representation of the product is as follows: SOD~~PHEG~~S-S-Py.

EXAMPLE 35—coupling of SOD~~PHEG~~S-S-Py with a RGD-peptide

The product of example 34 is dissolved in a 0.1 M phosphate buffer (10 mg/ml), pH 7,5. A RGD-peptide (HS-Cys-Gly-Arg-Gly-Asp-Ser-CONH$_2$) is dissolved in the same buffer (10 mg/ml, two-fold excess with respect to the S-S-Py moiety) and added to the above solution. The release of pyridine-2-thione, measured by ultraviolet spectroscopy, is used for determination of the end of the reaction (about 1 hour). The product is purified by using an Amicon ultrafiltration system with a PM-10 membrane and lyophilized. A schematic representation of the product is as follows: SOD~~PHEG~~RGD-peptide EXAMPLE 36—synthesis of a PHEG derivative conjugated with a poly-L-lysine (PLL-g-PHEG) and covalently bound to a RGD-peptide a) coupling of NHS~~PHEG~~S-S-Py with poly-L-lysine 1 g poly-L-lysine ($M_n$=20,000) is dissolved in 20 ml of a 0.1 M phosphate buffer pH 7,4. NHS~~PHEG~~S-S-Py (from 15.2) is dissolved in the same buffer and added to the solution. After stirring for 1 hr at room temperature, the mixture is separated on Sephadex G-25 (water as eluent). PLL-g-PHEG is isolated by lyophilization. $^1$H NMR (D$_2$O) analysis shows 10 and 20 mol % grafted PHEG on the PLL chain.

b) coupling of PLL-g-PHEG~~S-S-Py with an RGD-peptide

The above polymer PLL-g-PHEG~~S-S-Py is dissolved in 0.1 M phosphate buffer (10 mg/ml), pH 7,5. A RGD-peptide (HS-Cys-Gly-Arg-Gly-Asp-Ser-CONH$_2$) is dissolved in the same buffer (10 mg/ml, two-fold excess with respect to the S-S-Py moiety) and added to the above solution. The release of pyridine-2-thione, measured by ultraviolet spectroscopy, is used for determinating the end of the reaction (about 1 hour). The product is purified by using an Amicon ultrafiltration system with a PM-10 membrane and lyophilized. A schematic representation of the product is as follows: PLL-g-PHEG~~RGD.

EXAMPLE 37—synthesis of a block copolymer of poly-γ-hydroxyethyl-L-glutamine with polyglycolic acid a) synthesis of polyglycolic acid with hydroxyl groups at both ends of the polymer chain A silanized glass tube is charged with 1 g glycolide (9 mmole), 0.02 g 1,6-hexanediol (0.18 mmole) and two drops of stannous octoate. The tube is degassed, sealed under an argon blanket and placed in a thermostated oil bath at temperature 120–130° C. After 15 hours, polymerization is terminated by cooling to 4° C. The resulting polyglycolic acid (hereinafter referred to as PGA) is isolated by dissolving the reaction mixture in dichloromethane, followed by precipitation in hexane, then recrystallized from dichloromethanelmethanol and dried under vacuum. Its molecular weight, determined by gel permeation chromatography using polystyrene standard and tetrahydrofuran as eluent, is $M_n$=10,000 and its hydroxyl functionality, determined by $^1$H NMR, is 2. $^1$H NMR (CDCl$_3$) confirms the following structure of the polymer:

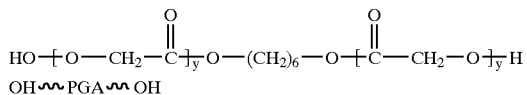

b) coupling of poly-γ-hydroxyethyl-L-glutamine with amino end group with polyglycolic acid 1 g polyglycolic acid obtained in step (a) is first activated, according to the scheme hereunder, by dissolving in 20 ml dichloromethane and adding 0.04 g carbonyidiimidazole (1.3 molar excess with respect to hydroxyl groups). The solution is stirred under reflux for 12 hours, then diluted with 20 ml dichloromethane and washed with water. The dichloromethane-layers are collected and dried over magnesium sulphate, the solvent is evaporated and the resulting product dried under vacuum.

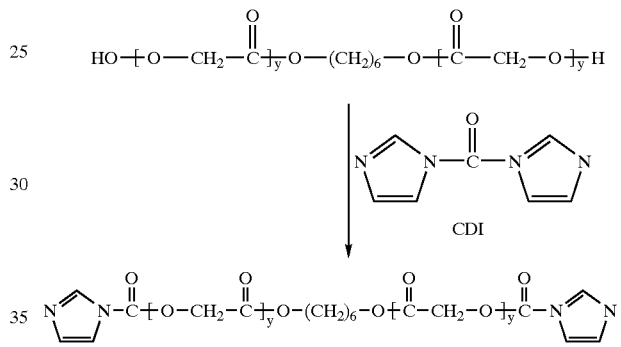

$^1$H NMR (CDCl$_3$) confirms the above structure of the activated polymer.

c) coupling of activated PGA with PHEG-NH$_2$ 1 g of the activated polymer prepared in step (b) is dissolved in 30 ml N,N-dimethylformamide. 0.97 g of the polymer of example 3 is dissolved in 40 ml N,N-dimethylformamide and added to the solution of activated PGA. The mixture is stirred at 60° C. for 24 hours, then part of the solvent is removed under vacuum and the resulting product is precipitated in pentane, filtered and dried under vacuum. The structure of the polymer (PHEG~~PGA~~PHEG) is confirmed by $^1$H NMR (DMF-d$_7$) analysis.

EXAMPLE 38—synthesis of a branched poly-γ-hydroxyethyl-L-glutamine

In this example, a modified L-lysine containing two primary amino groups is used as an initiator for the polymerization of an N-carboxyanhydride of γ-hydroxyethyl-L-glutamate.

a) synthesis of a bifunctional modified L-lysine

This synthesis proceeds according to the scheme shown hereinafter. 1 g L-lysine terbutyl ester (4,9 mmole) is dissolved in 10 ml dichloromethane and cooled to 0° C., then a solution of 3.5 g of a fluorenylmethyloxycarbonyl-protected 6-aminocaproic acid (9.8 mmole) in 20 ml dichloromethane is added. 2.02 g Dicyclocarbodiimide (9,8 mmole) is added and the solution is stirred for 1 hour at 0° C. and overnight at room temperature. The precipitated dicyclohexylurea is filtered and the filtrate is precipitated in hexane. The resulting product 3 (structure confirmed by $^1$H NMR (CDCl$_3$) analysis) is filtered and dried under vacuum.

1 g of product 3 is dissolved in 10 ml N,N-dimethylformamide and 10 ml of a 10% solution of piperidine in N,N-dimethylformamide is added. After stirring for 1 hour at room temperature, the solvent is removed under vacuum and the residue is triturated with ether, filtered and dried under vacuum. $^1$H NMR (CDCl$_3$) analysis confirms the structure of product 4.

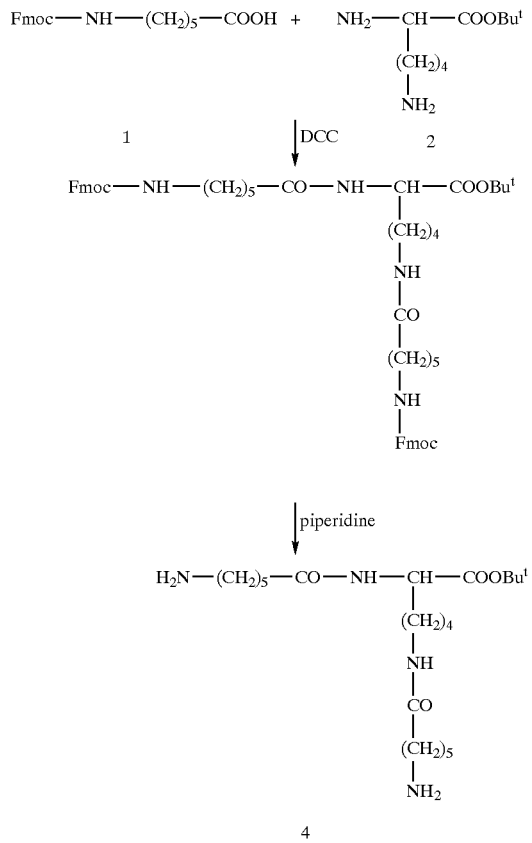

b) polymerization of N-carboxyanhydride of γ-trichloroethyl-L-glutamate using modified L-lysine as an initiator and acetic anhydride as a terminating agent 1 g N-carboxyanhydride of γ-trichloroethyl-L-glutamate (TCEG-NCA) is dissolved in 10 ml 1,2-dichloroethane and the solution is cooled to 10° C. 0.024 g of the modified L-lysine from step (a) is dissolved in 2 ml 1,2-dichloroethane and added under stirring to the solution of TCEG-NCA. After the end of polymerization, determined by infrared spectroscopy (about 3 hours), acetic anhydride (6-fold molar excess with respect to the initator) and an equimolar amount of triethylamine are added and the reaction mixture is stirred for another 2 hours at room temperature. The solution is precipitated in pentane and the resulting polymer is isolated by filtration and dried under vacuum. Its molecular weight, determined by $^1$H NMR (DMF-d$_7$), is Mn=10,500. $^1$H NMR (DMF-d$_7$) analysis confirms the following structure of the polymer:

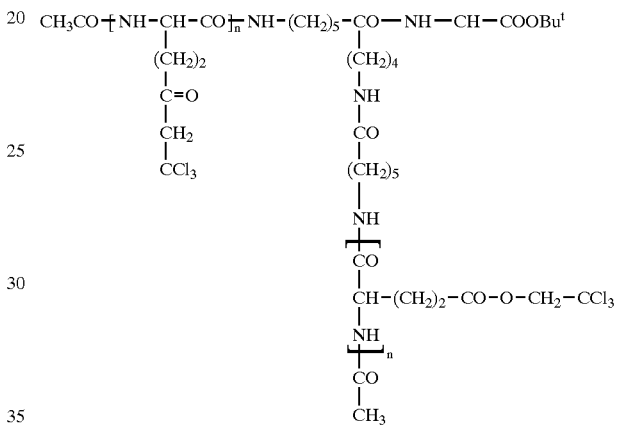

c) aminolysis of a branched poly-γ-hydroxyethyl-L-glutamate with ethanolamine

Aminolysis of the branched poly-γ-hydroxyethyl-L-glutamate from step (b) is carried out and the product is isolated and characterised as already described in example 2. $^1$H NMR (D$_2$O) analysis confirms the following structure of the polymer:

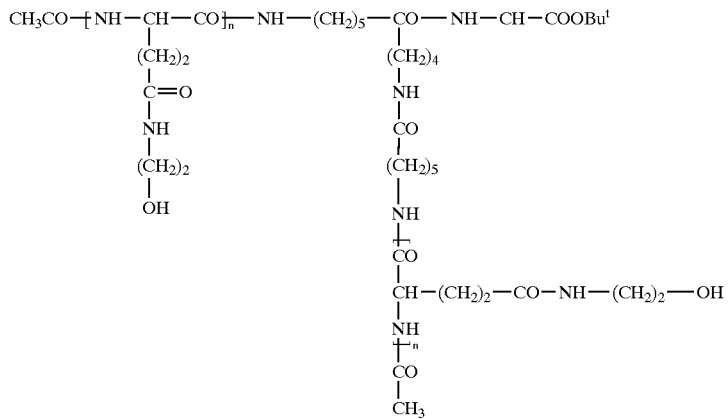

d) deprotection of the tert-butyl group on a branched poly-γ-hydroxyethyl-L-glutamine 1 g of the polymer obtained in step (b) is dissolved in 10 ml trifluoroacetic acid and stirred at room temperature for 1 hour. Trifluoroacetic acid is removed under vacuum. The polymer is dissolved in water and centrifugated. The supernatant is purified by gel filtration on Sephadex G-25 (water as eluent), then the resulting product is isolated by lyophilization. $^1$H NMR (D$_2$O) analysis confirms the following structure of the polymer:

EXAMPLE 40—synthesis of a branched poly-γ-hydroxyethyl-L-glutamine

This example illustrates the "activated monomer process" route followed by termination with a modified L-lysine, according to the scheme represented hereinafter.

2 g of an N-carboxyanhydride of γ-trichloroethyl-L-glutamate (TCEG-NCA) is dissolved in 20 ml dichlo-

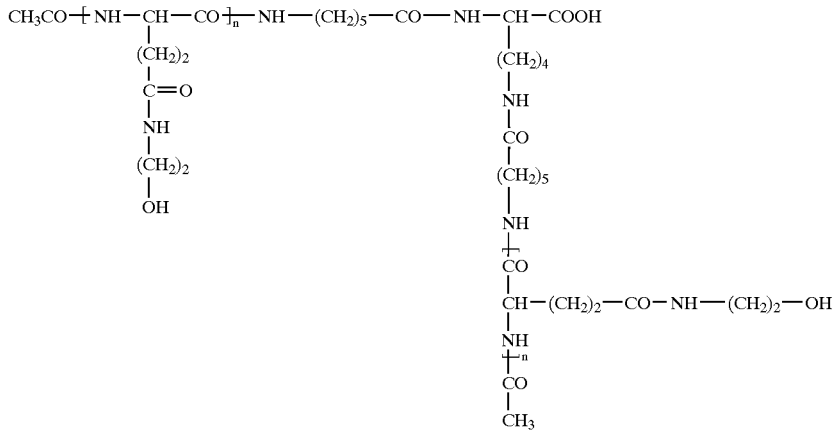

EXAMPLE 39—coupling of a branched poly-γ-hydroxyethyl-L-glutamine

The branched poly-γ-hydroxyethyl-L-glutamine obtained in example 38 can be coupled via its reactive carboxylic acid end group with a protein, peptide, enzyme (such as SOD) or cationic polymer containing amino groups while using the methods of examples 34 to 36. Schematic representations of products which can thus be obtained are as follows:

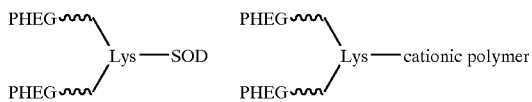

romethane. Solutions of 0.114 g N-acetylated TCEG-NCA (5 mole % with respect to TCEG-NCA) in 5 ml dichloromethane and 0.06 g tributylamine (5 mole % with respect to TCEG-NCA) in 2 ml dichloroethane are then added to the solution of TCEG-NCA. After the end of the polymerization (about 3 hours), determined by infrared spectroscopy, a solution of 3.9 g of the modified L-lysine from example 38 in 5 ml dichloromethane is added and the reaction mixture is stirred for another 3 hours at room temperature. The solution is precipitated in pentane and the resulting polymer is isolated by filtration and dried under vacuum. Its molecular weight determined by $^1$H NMR (DMF-d$_7$) is 12,000. $^1$H NMR (DMF-d$_7$) confirms the structure of polymer 6 of the following scheme.

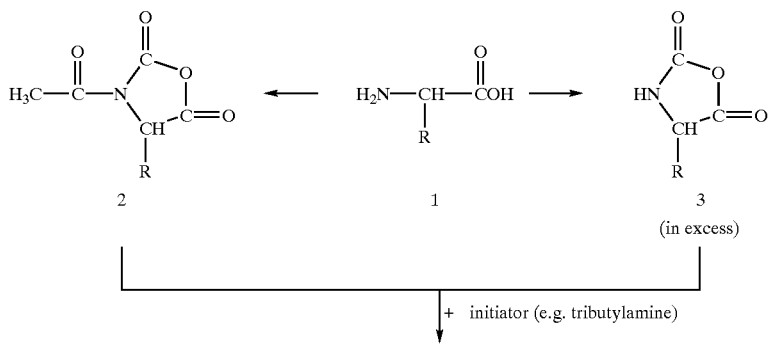

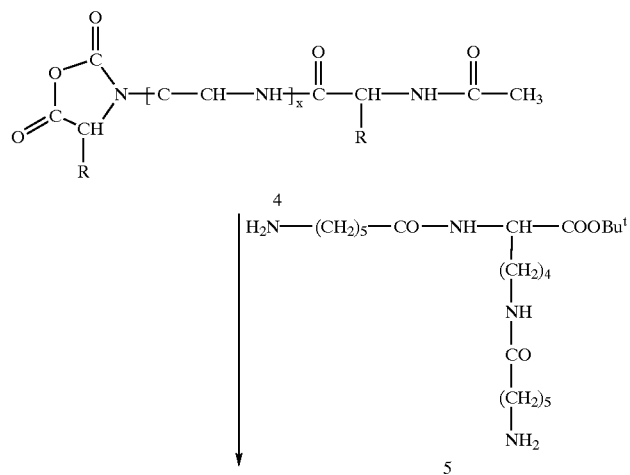

4

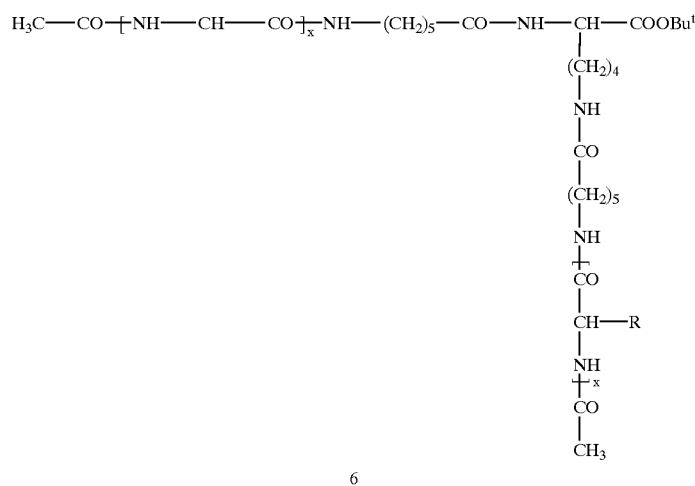

6 where R=(CH$_2$)$_2$—CO—O—CH$_2$—CCl$_3$

H$_3$C—CO—[NH—CH—CO]$_x$—NH—(CH$_2$)$_5$—CO—NH—CH—COOBu$^t$ (with R branch and (CH$_2$)$_4$—NH—CO—(CH$_2$)$_5$—NH—[CO—CH—R—NH]$_x$—CO—CH$_3$)

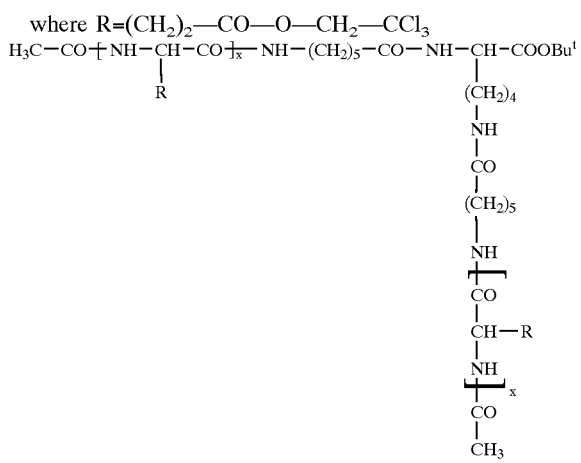

where R=(CH$_2$)$_2$—CO—NH—CH$_2$—OH

Aminolysis of the branched poly-γ-hydroxyethyl-L-glutamate with ethanolamine is then carried out and the product is isolated and characterised as already described in Aminolysis of the branched poly example 2. $^1$H NMR (D$_2$O) analysis confirms the above polymer structure.

Deprotection of the tert-butyl group on the branched poly-γ-hydroxyethyl-L-glutamine is performed as in example 38. $^1$H NMR (D$_2$O) analysis confirms the following polymer structure:

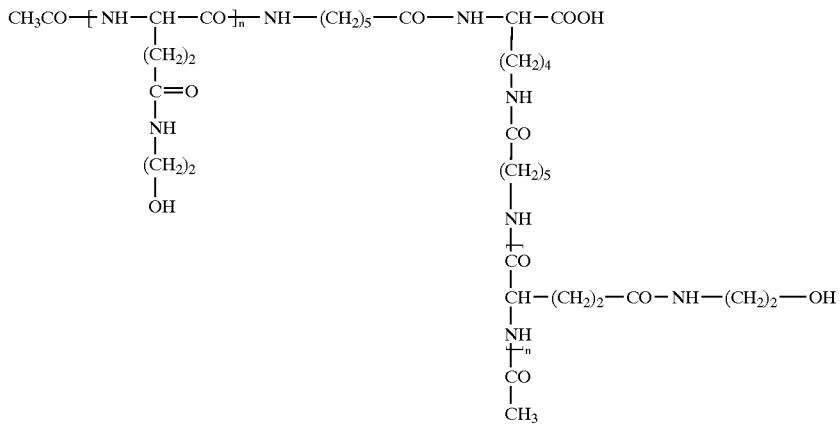

What is claimed is:

1. A linear monofunctional or multifunctional poly-α-amino-acid derivative having at least glutamic or aspartic or serinic repeating units in the polymer backbone, the said glutamic or aspartic or serinic repeating units having the formula:

—CO—CHR—NH— (I)

wherein:
R is defined as —(CH$_2$)$_n$—CO—OR$_1$ or —(CH$_2$)$_n$—CO—NHR$_2$ or CH$_2$OH,
n is 1 or 2, —R$_1$ is selected from hydrogen, C$_{1-20}$alkyl, polyhaloC$_{1-6}$alkyl, arylC$_{1-6}$ alkyl and heteroarylC$_{1-6}$alkyl, and
R$_2$ is C$_{1-6}$alkyl substituted with at least one alcohol group, characterized in additionally having a functional group at one or both ends of the polymer backbone, the said functional end group(s) being selected from the group consisting of functionalized amines, N-acyl, ester, carbonate, thiol, thiol precursor, thioisocyanate, thiocarbonate, urea, thiourea, aldehyde, acetal, N-carboxyanhydride, oxycarbonyl, maleimide and any vinyl group suitable for radical, anionic or cationic polymerization.

2. A linear multifunctional poly-α-amino-acid derivative according to claim 1, having a functional group at both ends of the polymer backbone, and additionally having a single functional group as a side group.

3. A linear poly-α-amino-acid derivative according to claim 1, additionally comprising repeating units of one or more comonomer(s) copolymerizable with the α-amino-acid sequence containing glutamic or aspartic or serinic repeating units.

4. A linear poly-α-amino-acid derivative according to claim 1, additionally comprising repeating units of one or more comonomer(s) copolymerizable with the α-amino-acid sequence containing glutamic or aspartic or serinic repeating units, wherein the said co-monomer is selected from the group consisting of any naturally-occurring α-amino-acid other than glutamic acid, aspartic acid and serine and polymer blocks or sequences derived from ethylene oxide or propylene oxide or polyhydroxyalkanoates.

5. A linear poly-α-amino-acid derivative according to claim 1, being multifunctional and having any of the following formulae:

V—[CO—CHR—NH]$_x$—[A]$_y$—W (IIa)

V—[A]$_y$—[CO—CHR—NH]$_{x'}$—W (IIb)

V—[CO—CHR—NH]$_x$—[A]$_y$—[CO—CHR—NH]$_x$—W (IIc)

V—[CO—CHR—NH]$_x$—T—[CO—CHR—NH]$_{x'}$—V
                                  |
                                  W (IId)

V—[CO—CHR—NH]$_x$—T—[CO—CHR—NH]$_{x'}$—V'
                                  |
                                  W (IIe)

wherein:
R is as defined in claim 1,
x or, where applicable, x+x' range from 2 to 2,000,
each of V and W independently represent a functional group,
A is at least a co-monomer copolymerizable with the α-amino-acid sequence containing glutamic or aspartic or serinic repeating units,
y ranges from 0 to 500,
T is a spacing unit selected from lysine and ornithine, and
V' is a non-reactive end group.

6. A linear poly-α-amino-acid derivative according to claim 1, being monofunctional and having any of the following formulae:

V—[CO—CHR—NH]$_x$—[A]$_y$—W' (Va)

V$^1$—[CO—CHR—NH]$_x$—[A]$_y$—W (Vb)

V—[CO—CHR—NH]$_x$—[A]$_y$—[CO—CHR—NH]$_{x'}$—W$^1$ (Vc)

V$^1$—[CO—CHR—NH]$_x$—[A]$_y$—[CO—CHR—NH]$_{x'}$—W (Vd)

V$^1$—[CO—CHR—NH]$_x$—T—[CO—CHR—NH]$_{x'}$—V'
                                  |
                                  W (VI)

wherein:
R is as defined in claim 1,
x or, where applicable, x+x' range from 2 to 2,000, and each of V and W independently represent a functional group, A is at least a co-monomer copolymerizable with the α-amino-acid sequence containing glutamic or aspartic or serinic repeating units, y ranges from 0 to 500, T is a spacing unit selected from lysine and ornithine, and V' and W' are non-reactive end groups.

7. A linear poly-α-amino-acid derivative according to claim 1, having at least one protective end group and being represented by the following formulae:

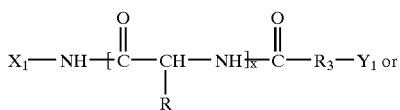
(VII),

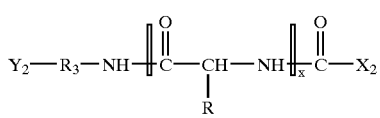
(VIII), wherein:

R is —$(CH_2)_n$—CO—$NHR_2$, $R_2$ and n are as defined in claim 1, x ranges from 2 to 2,000, $X_1$ is —$R_4$—$Z_1$—$A_1$, each of $R_3$ and $R_4$ is independently selected from $(CH_2)_m$, arylene, $C_{1-6}$ alkylarylene and arylCl$_{1-6}$alkylene, m is from 2 to 20, $Y_1$ is —$Z_2$—$A_2$, $X_2$ is —$R_4$—$Z_3$—$A_3$ or —O—$R_4$—$Z_3$—$A_3$, $Y_2$ is —$Z_4$—$A_4$, each of $Z_1$, $Z_2$, $Z_3$ and $Z_4$ is independently selected from NH, O, S, C(O)O, C(S)O, CO, CS, —OCH—O— and C=N—$R_5$, each of $A_1$, $A_2$, $A_3$ and $A_4$ is a protective group suitable for $Z_1$, $Z_2$, $Z_3$ and $Z_4$ respectively, and $R_5$ is selected from hydrogen, $C_{1-6}$alkyl, aryl and $C_{1-6}$alkylaryl, heteroaryl and $C_{1-6}$alkylheteroaryl.

8. A linear poly-α-amino-acid derivative according to claim 1, being represented by the formula:

$X_1$—NH-[CO—CHR—NH]$_x$—CO—CHR—$NH_2$ (IX)

wherein:

$X_1$ is —$R_4$—$Z_1$—$A_1$, $R_4$ is selected from the group consisting of $(CH_2)_m$, arylene, $C_{1-6}$ alkylarylene and arylC$_{1-6}$alkylene, m is from 1 to 20, x ranges from 2 to 2,000, R is defined as —$(CH_2)_n$—CO—$OR_1$, $R_1$ and n are as defined in claim 1, $Z_1$ is selected from the group consisting of NH, O, S, C(O)O, C(S)O, CO, CS, —OCH—O— and C=N—$R_5$, $A_1$ is a protective group suitable for $Z_1$, and $R_5$ is selected from the group consisting of hydrogen, $C_{1-6}$alkyl, aryl, $C_{1-6}$ alkylaryl, heteroaryl and $C_{1-6}$alkylheteroaryl.

9. A linear poly-α-amino-acid derivative according to claim 1, being represented by any of the respective formulae:

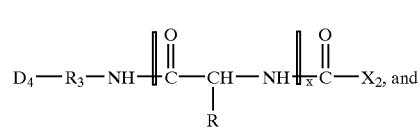
(X)

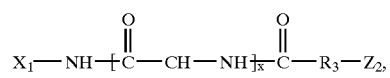
(XI)

wherein:

R is —$(CH_2)_n$—CO—$NHR_2$, $R_2$ and n are as defined in claim 1, x ranges from 2 to 2,000, $X_1$ is —$R_4$—$Z_1$—$D_1$, each of $R_3$ and $R_4$ is independently selected from the group consisting of $(CH_2)_m$, arylene, $C_{1-6}$alkyl-arylene and aryl-$C_{1-6}$alkylene, m is from 2 to 20, each of $R_3$—$Y_1$ and $R_3$—$Y_2$ is a group including a vinyl terminal moiety, $X_2$ is —$R_4$—$Z_3$—$D_3$, each of $Z_1$, $Z_2$, $Z_3$ and $Z_4$ is independently selected from the group consisting of NH, O, S, C(O)O, C(S)O, CO, CS, —OCH—O— and C=N—$R_5$, each of $D_1$, $D_2$, $D_3$ and $D_4$ is independently selected from the group consisting of hydrogen, aryl, heteroaryl, succinimidyl, vinyl and $C_{1-6}$alkylcarbonyl, each of $Z_1$—$D_1$, $Z_2$—$D_2$, $Z_3$—$D_3$ and $Z_4$—$D_4$ is independently selected from the group consisting of maleimidyl, disulfide, α-haloacetoxy and $C_{1-6}$alkyloxymethylsulfide, and $R_5$ is selected from the group consisting of hydrogen, $C_{1-6}$alkyl, aryl, $C_{1-6}$ alkyl-aryl, heteroaryl and $C_{1-6}$alkyl-heteroaryl.

10. A process for making a linear monofunctional or multifunctional poly-α-amino-acid derivative having at least glutamic or aspartic or serinic repeating units in the polymer backbone and additionally having a functional group at one or both ends of the polymer backbone, the said functional end group(s) being selected from the group consisting of functionalized amines, N-acyl, ester, carbonate, thiol, thiol precursor, thioisocyanate, thiocarbonate, urea, thiourea, aldehyde, acetal, N-carboxyanhydride, oxycarbonyl, maleimide and any vinyl group suitable for radical, anionic or cationic polymerization, said process including a step comprising polymerizing a monomer or mixture of monomers comprising at least the N-carboxy anhydride of an amino-acid selected from the group consisting of glutamic acid, aspartic acid, serine and oxygen-protected serine, wherein said polymerization is effected in the presence of an effective amount of a multifunctional initiator containing at least one primary amino group and further containing at least another functional group selected from maleimide, thioisocyanate, thiocarbonate, urea, thiourea, aldehyde, acetal, oxycarbonyl, vinyl, ester, carbonate, thiol precursor, protected amine and protected carboxylic acid and/or in the presence of an effective amount of a bi-functional terminating reagent.

11. A process according to claim 10, further including aminolysis of the pending group of the glutamic, aspartic or serinic repeating unit derived from glutamic acid, asparic acid or serine by means of an effective amount of an amino-alcohol, in the presence of an effective amount of a reaction promoter.

12. A process for making a linear monofunctional or multfunctional poly-α-amino-acid derivative having at least glutamic or aspartic or serinic repeating units in the polymer backbone and additionally having a functional group at one or both ends of the polymer backbone, the said functional end group(s) being selected from the group consisting of functionalized amines, N-acyl, ester, carbonate, thiol, thiol precursor, thiosocyanate, thiocarbonate, urea, thiourea, aldehyde, acetal, N-carboxyanhydride, oxycarbonal, maleimide and any vinyl group suitable for radical, anionic or cationic polymerization, said process including:

a first step of N-acylating part of an α-amino-acid selected from the group consisting of glutamic acid, aspartic acid and serine, then separately treating the N-acylated α-amino-acid and the remaining part of the said α-amino-acid in order to form a mixture of the corresponding N-carboxy anhydrides, and a second step of copolymerizing the said mixture of N-carboxy anhydrides in the presence of an initiator.

13. A process according to claim 12, wherein the N-carboxy anhydride terminated polymer obtained in the second step is reacted with a reagent having the formula H$_2$N—R$_3$—Y$_2$, wherein:

R$_3$ is selected from the group consisting of (CH$_2$)$_m$, arylene, C$_{1-6}$ alkylarylene and arylC$_{1-6}$alkylene, m is from 2 to 20, Y$_2$ is —A$_4$, Z$_4$ is selected from the group consisting of NH, O, S, C(O)O, C(S)O, CO, CS, —OCH—O— and C=N—R$_5$, A$_4$ is a protective group suitable for Z$_4$, and R$_5$ is selected from the group consisting of hydrogen, C$_{1-6}$alkyl, aryl, C$_{1-6}$alkylaryl, heteroaryl and C$_{1-6}$alkylheteroaryl.

14. A biodegradable article containing a copolymer comprising at least a moiety derived from a linear monofunctional or multifunctional poly-α-amino-acid derivative having at least glutamic or aspartic or serinic repeating units in the polymer backbone and additionally having a functional group at one or both ends of the polymer backbone, the said functional end group(s) being selected from the group consisting of functionalized amines, N-acyl, ester, carbonate, thiol, thiol precursor, thioisocyanate, thiocarbonate, urea, thiourea, aldehyde, acetal, N-carboxyanhydride, oxycarbonyl, maleimide and any vinyl group suitable for radical, anionic or cationic polymerization, and wherein the said functional end group(s) is an unsaturated group.

15. A poly-α-amino-acid derivative according to claim 1, containing a L-amino-acid sequence and being enzymatically degradable.

16. A linear mono-functional or multifunctional poly-α-amino-acid derivative having at least glutamic or aspartic or serinic repeating units in the polymer backbone, the said glutamic or aspartic or serinic repeating units having the formula:

—CO—CHR—NH— (I)

wherein:

R is defined as —CH$_2$)$_n$—CO—OR$_1$ or —CH$_2$)$_n$—CO—NHR$_2$ or CH$_2$OH, n is 1 or 2, R$_1$ is selected from the group consisting of hydrogen, C$_{1-20}$alkyl, polyhalo-C$_{1-6}$alkyl, aryl-C$_{1-6}$alkyl and heteroaryl-C$_{1-6}$alkyl, and R$_2$ is C$_{1-6}$alkyl substituted with at least one alcohol group, said poly-α-amino-acid derivative additionally having a functional group at one or both ends of the polymer backbone, said functional end group(s) being other than alcohol, said poly-α-amino-acid derivative containing a D-amino-acid sequence and being non-degradable.

17. The product of coupling a biomolecule with a linear monofunctional or multifunctional poly-α-amino-acid derivative having at least glutamic or aspartic or serinic repeating units in the polymer backbone and additionally having a functional group at one or both ends of the polymer backbone, the said functional end group(s) being selected from the group consisting of functionalized amines, N-acyl, ester, carbonate, thiol, thiol precursor, thioisocyanate, thiocarbonate, urea, thiourea, aldehyde, acetal, N-carboxyanhydride, oxycarbonyl, maleimide and any vinyl group suitable for radical, anionic or cationic polymerization.

18. The product of claim 17, wherein the said biomolecule is selected from the group consisting of therapeutic agents, prophylactic agents, diagnostic agents, proteins, peptides, hormones, antibodies and fragments thereof, oligonucleotides, plasmids, DNAs, interleukins, interferons and enzymes and fragments thereof.

19. A synthetic polymer for a polymer-based carrier vehicle or vector for delivery of DNA or other nucleic acid material to target cells in a biological system, comprising a linear monofunctional or multifunctional poly-α-amino-acid derivative having at least glutamic or aspartic or serinic repeating units in the polymer backbone and additionally having a functional group at one or both ends of the polymer backbone, the said functional end group(s) being selected from the group consisting of functionalized amines, N- acyl, ester, carbonate, thiol, thiol precursor, thioisocyanate, thiocarbonate, urea, thiourea, aldehyde, acetal, N-carboxyanhydride, oxycarbonyl, maleimide and any vinyl group suitable for radical, anionic or cationic polymerization.

20. A synthetic polymer for a polymer-based carrier vehicle or vector according to claim 19, further comprising a synthetic vector component such as polyethyleneimine, poly-L-lysine, a star-shaped dendrimer or chitosan.

21. A method of treatment of a patient in need of such treatment, comprising administration to said patient of a biologically-active ingredient modified by or a nucleic acid material carried by a polymer system comprising a linear monofunctional or multifunctional poly-α-amino-acid derivative having at least glutamic or aspartic or serinic repeating units in the polymer backbone and additionally having a functional group at one or both ends of the polymer backbone, the said functional end group(s) being selected from the group consisting of functionalized amines, N-acyl, ester, carbonate, thiol, thiol precursor, thioisocyanate, thiocarbonate, urea, thiourea, aldehyde, acetal, N-carboxyanhydride, oxycarbonyl, maleimide and any vinyl group suitable for radical, anionic or cationic polymerization.

22. A linear mono-functional or multifunctional poly-α-amino-acid derivative according to claim 16, wherein said functional end group(s) are selected from the group consisting of functionalized amines, N-acyl, ester, carbonate, thiol, thiol precursor, thioisocyanate, thiocarbonate, urea, thiourea, aldehyde, acetal, N-carboxyanhydride, oxycarbonyl, maleimide.

* * * * *